United States Patent
McHale et al.

(10) Patent No.: US 6,821,274 B2
(45) Date of Patent: Nov. 23, 2004

(54) ULTRASOUND THERAPY FOR SELECTIVE CELL ABLATION

(75) Inventors: Anthony Patrick McHale, Coleraine (IE); Anna Maria Rollan Haro, Coleraine (IE)

(73) Assignee: Gendel Ltd., Londonderry (IE)

( * ) Notice: Subject to any disclaimer, the term of this patent is extended or adjusted under 35 U.S.C. 154(b) by 68 days.

(21) Appl. No.: 10/113,173

(22) Filed: Mar. 29, 2002

(65) Prior Publication Data

US 2002/0193784 A1 Dec. 19, 2002

Related U.S. Application Data

(60) Provisional application No. 60/279,812, filed on Mar. 29, 2001, and provisional application No. 60/322,388, filed on Sep. 14, 2001.

(30) Foreign Application Priority Data

| Mar. 7, 2001 | (GB) | ................................................ 105643 |
| Aug. 23, 2001 | (GB) | ................................................ 120582 |
| Nov. 16, 2001 | (GB) | ................................ PCT/GB01/05065 |

(51) Int. Cl.[7] .............................................. A61B 18/18
(52) U.S. Cl. ......................... 606/41; 606/28; 435/173.1
(58) Field of Search .............................. 606/1, 27, 28, 606/41; 604/21, 22; 435/461, 450, 173.1, 173.4–173.6

(56) References Cited

U.S. PATENT DOCUMENTS

| 4,888,746 | A |   | 12/1989 | Wurster et al. | ............. 367/138 |
| 5,895,356 | A |   | 4/1999 | Andrus et al. | ............... 600/439 |
| 5,938,608 | A |   | 8/1999 | Bieger et al. | ............... 600/439 |
| 6,041,253 | A | * | 3/2000 | Kost et al. | ..................... 604/20 |
| 6,190,380 | B1 | * | 2/2001 | Abela | ........................... 606/28 |
| 6,251,110 | B1 | * | 6/2001 | Wampler | ..................... 606/49 |
| 6,533,803 | B2 | * | 3/2003 | Babaev | ......................... 607/89 |
| 2001/0007666 | A1 | * | 7/2001 | Hoffman et al. | ............ 424/400 |
| 2001/0008758 | A1 | * | 7/2001 | McHale et al. | ................. 435/2 |
| 2001/0053549 | A1 | * | 12/2001 | McHale et al. | ............. 435/446 |
| 2002/0009706 | A1 | * | 1/2002 | McHale et al. | ................ 435/2 |
| 2003/0229283 | A1 | * | 12/2003 | Craig et al. | ................. 600/439 |

FOREIGN PATENT DOCUMENTS

| WO | WO 97/18855 | 5/1997 | ............ A61N/1/30 |
| WO | WO 97/35518 | 10/1997 | ............ A61B/5/08 |
| WO | WO 97/40679 | 11/1997 | .......... A01N/43/04 |
| WO | WO 99/01157 | 1/1999 | .......... A61K/48/00 |
| WO | WO 99/01158 | 1/1999 | .......... A61K/48/00 |
| WO | WO 99/06101 | 2/1999 | ............ A61N/1/04 |
| WO | WO 99/22652 | 5/1999 | ........... A61B/17/22 |
| WO | WO 99/22809 | 5/1999 | ............ A61N/1/30 |
| WO | WO 01/07011 | 2/2001 | ............ A61K/9/00 |

OTHER PUBLICATIONS

International Search Report of Application No. GB 0213631.5.

Hildebrandt, G., et al. (1998), "Effects of Low Dose Ionizing Radiation on Murine Chronic Granulomatous Tissue," *Strahlenther Onkol*, 174:580–588.

Longstaff, E., et al. (2001), "Condyloma Eradication: Self–Therapy with 0.15–0.5% Podophyllotoxin versus 20–25% Podophyllin Preparations—An Integrated Safety Assessment," *Reg. Tox. Pharm.* 83:117–137.

Nordenstrom, B. (1989), "Electrochemical Treatment of Cancer. I: Variable Response to Anodic and Cathodic Fields," *Am. J. Clin. Oncol.*, 12:530–536.

Wojcicki, M., et al. (2000), "Antitumor effect of electro–chemical therapy on transplantable mouse cancers," *Med Sci. Monit.*, 6:498–502.

* cited by examiner

*Primary Examiner*—Michael Peffley
(74) *Attorney, Agent, or Firm*—Frommer Lawrence & Haug, LLP; Thomas J. Kowalski; Deborah Lu

(57) ABSTRACT

The invention provides a method of sensitizing target cells to ultrasound energy using a stimulus such as an electric field. This "electrosensitisation" enables target cells to be disrupted by ultrasound at frequencies and energies of ultrasound which do not cause disruption of non-sensitized (i.e., non-target) cells. As a consequence, the method increases the selectivity of ultrasound therapy, providing a way to ablate undesired cells, such as diseased cells (e.g., tumor cells) while minimizing harm to neighboring cells. In another aspect, however, ultrasound can be used to sensitize cells while the electrical field is used to disrupt cells. The invention also provides an apparatus for performing the method and assays for identifying gene products and other molecules involved in apoptosis.

12 Claims, 13 Drawing Sheets

C          T

Positive control

ULTRASOUND THERAPY FOR SELECTIVE CELL ABLATION

PRIORITY

The present application claims priority under 35 U.S.C. §119(e) to U.S. Provisional Application Ser. No. 60/279,812, filed Mar. 29, 2001, and U.S. Provisional Application Ser. No. 60/322,388, filed Sep. 14, 2001, and also claims priority under 35 U.S.C. §120 to International Application Number PCT/GB01/05065, filed Nov. 16, 2001, which claims priority to GB0105643.1, filed Mar. 7, 2001, and GB0120582.2, filed Aug. 23, 2001, the entireties of which are incorporated herein by reference.

FIELD OF THE INVENTION

The present invention relates to the use of a combination of electric field energy and ultrasound energy for the selective ablation of tissues, such as tumor tissues, and preferably cells in an organism.

BACKGROUND TO THE INVENTION

In general therapeutic applications of ultrasound in the clinic may be divided into two major categories; applications that employ low intensity (0.125–3 W/cm$^2$) and those that employ higher intensities ($\geq$5 W/cm$^2$) (ter Haar, 1999, *Eur. J. Ultrasound* 9: 3). Low intensity ultrasound is commonly used in applications such as physiotherapy, for example, to stimulate normal physiological responses to injury or to accelerate processes, such as the transport of drugs across the skin. Treatment with low intensity ultrasound rarely results in collateral tissue damage and usually extreme efforts are employed to minimise such effects. This includes minimising excessive tissue heating which results from exposure to ultrasound, typically by reducing the treatment time and/or delivering the ultrasound in a pulsed manner.

In contrast, the major objective of applications involving the use of high intensity ultrasound is to selectively destroy tissue by hyperthermic processes. High intensity ultrasound-mediated tissue ablation may be categorised according to the way in which ultrasound energy is delivered to tissues. Ultrasound may be delivered directly from a transducer to the treatment area; alternatively, a coupling device which focuses the ultrasound may mediate delivery. When provided through a coupling device, ultrasound passing through intervening tissues is usually low intensity and therefore, relatively non-destructive. However, at the focal point, the energy which has accumulated is raised to a pre-determined higher intensity and tissue destruction occurs at, or around, the focal point. Thus, using a coupling device has the advantage of selectively delivering ablative energy to a tissue being treated without causing major damage to intervening tissues.

In general, therapeutic applications which rely on the use of high intensity focussed ultrasound, or "HIFU," exploit the heat which is generated at the focal point and a number of methods together with devices for achieving focus and tissue ablation have been suggested (see, e.g., U.S. Pat. Nos. 4,888,746; 5,895,356; 5,938,608 and International Patent Applications WO 97/35518 A1 and WO 99/22652 A1).

In addition to a requirement for relatively sophisticated equipment to achieve focussing of high intensity ultrasound, one major disadvantage associated with the use of HIFU involves the potential for the occurrence of cavitation events which, in turn, leads to the formation of destructive, or possibly mutagenic, free radicals (Miller et al., (1996) *Ultrasound in Med. & Biol.* 22: 1131). An alternative approach involving a mechanism of sensitising the target tissue to low intensity ultrasound (either focussed or non-focussed) would therefore provide an advantage.

It has been found that the delivery of short, intense electric pulses to cell populations or tissues in vivo results in transient permeabilisation of cell membranes and this has provided the basis for what has become known as electro-chemotherapy (Heller et al., (1999) *Advanced Drug Delivery Rev.* 35: 119). Electrochemotherapy was originally developed to facilitate the passage of chemotherapeutic drugs into cancer cells which had become impermeable to those drugs. The technique has developed to a stage where delivery of electric pulses in vivo is being exploited in areas such as gene therapy in order to mediate introduction of DNA to target tissues. Devices designed to facilitate delivery of electric pulses in vivo under a variety of conditions (e.g., transdermal, laparoscopic, catheter-mediated delivery, etc.) currently exist (see, e.g., International Patent Applications WO 99/22809 A1, WO 99/06101 A1; WO 99/01157 A1, WO 99/01157 A1, and WO 99/01158).

More recently, it has been found that exposure of human erythrocytes to short and intense electric pulses which facilitates transient permeabilisation also results in a dramatic sensitisation to low intensity ultrasound (WO 01/07011).

SUMMARY OF THE INVENTION

The present invention relies partially on the discovery that sensitisation of nucleated cells by application of an electric field ("electrosensitisation") renders the cells susceptible to ablation using low intensity ultrasound and thereby provides a means of eliminating unwanted cells and tissues in the body. The invention also relies on the discovery that exposure of a cell to ultrasound followed by exposure to electric fields also results in cell disruption. Thus, exposure of a nucleated cell to ultrasound and an electric field applied in any order, results in cell disruption.

In one aspect, the invention provides a method of rendering a cell sensitive to disruption by ultrasound comprising exposing the cell to an electric field for an amount and time sufficient to render it more susceptible to disruption by ultrasound than an unsensitised cell. The invention also provides a method of disrupting a cell comprising providing a cell which has been exposed to an electric field for an amount and time sufficient to render it more susceptible to disruption by ultrasound than an unsensitised cell; and exposing the cell to ultrasound, thereby disrupting the cell. The invention further provides a method of disrupting a cell comprising exposing the cell to an electric field for an amount and time sufficient to render it more susceptible to disruption by ultrasound than an unsensitised cell; and exposing said cell to ultrasound, thereby disrupting the cell. The cell can be part of a tissue, such as a tumor tissue, and exposure to ultrasound can be performed in vitro, ex vivo, or in vivo. Similarly, the step of exposing the cell to the electric field can occur in vitro, ex vivo, or in vivo. Disruption can be a result of apoptosis of the cell and in a preferred aspect, disruption results in ablation of cells from the body of an organism.

In one aspect, the method further comprises the step of exposing the cell to an agent which facilitates cell death. The cell-death facilitating agent can be selected from the group consisting of an oligonucleotide, a ribozyme, an antibody, an enzyme, a cytotoxic agent, a cytostatic agent, a cytokine, GM-CSF, IL-2, an immunogen, and combinations thereof.

In one aspect, the electric field to which the cell is exposed is from about 1 Volt/cm to 10 kVolts/cm. The electric field is preferably applied for between about 1 µs and 100 milliseconds. Ultrasound is preferably applied at a power level of from about 0.05 W/cm$^2$ to 100 W/cm$^2$ and continuous wave ultrasound or pulsed wave ultrasound can be applied.

In one aspect, the invention provides a method for disrupting a cell which comprises exposing the cell to a sensitising stimulus. The sensitising stimulus makes a cell more susceptible to a disrupting stimulus than a non-sensitised cell. The cell is then exposed the cell to a disrupting stimulus under conditions suited to disrupt the sensitised cell while not substantially disrupting non-sensitised cell.

In another aspect, the invention provides a method for selectively disrupting one or more target cells at a target site comprising a plurality of cells comprising: (a) exposing the one or more cells to an electric field; and (b) exposing the one or more cells to ultrasound; wherein the exposing in steps (a) and (b) disrupts the one or more target cells.

Preferably, the electric field is a low intensity electric field which has an electric field strength of less than 20 V/cm. In one aspect, direct current is applied to expose the one or more cells to the low intensity electric field. In another aspect, the current is between 100 µA to 200 mA.

In one aspect, the method is performed using an electric field is from 1 Volt/cm to 10 kVolts/cm under in vivo conditions. In another aspect, the electric field is applied for between 1 µs and 100 milliseconds. In a further aspect, ultrasound is applied at a power level of from 0.05 W/cm$^2$ to 100 W/cm$^2$. Ultrasound can be continuous wave ultrasound and pulsed wave ultrasound.

In one aspect, the one or more target cells comprise abnormally proliferating cells. For example, the one or more target cells can comprise tumor cells from a tumor which may be benign or malignant.

In another aspect, the one or more target cells are skin cells. The target site can comprise a wart, a papiloma, a psoriatic region of skin, a region of skin with eczema, or a mole.

In another aspect, the target site comprises a plurality of cells in a fluid, for example a buffer, cell culture medium or a bodily fluid. For example, the method can be performed at least partially in vitro, such as in a container or an extracorporeal circulating device. In another aspect, target site is within the body of an organism and the method is performed in situ. The target site can be exposed through an open surgical field or can be accessed using a medical access device which brings a source of electrical energy and ultrasound energy in sufficient proximity to the target site, to disrupt said one or more target cells.

The medical access device can be selected from the group consisting of a catheter, an endoscope, and a laparoscope.

The method can be used to remove unwanted cells for either therapeutic or cosmetic purposes. In one aspect, the target site comprises an unwanted fatty deposit, such as a lipoma and the one or more target cells comprise adipose cells.

Exposing in steps (a) and (b) can be performed over repeated intervals; for example, to remove a cell growth that may reoccur (e.g., such as a cancer).

Exposing can also be used to debulk tissue. In one aspect, the one or more cells are at the site of a wound. In another aspect, the one or more cells are within a blood vessel. In a further aspect, the target site comprises benign granulomatous tissue.

In one aspect, step (a) of the method comprises providing one or more pulses of electrical energy; preferably, multiple pulses are provided.

In another aspect, step (b) comprises providing low intensity ultrasound.

In one aspect, exposing in step (a) sensitises the one or more target cells and exposing in step (b) disrupts the one or more target cells. However, in another aspect, exposing in step (b) sensitises the one or more target cells and exposing in (a) disrupts the one or more target cells, and step (b) is performed prior to step (a).

In one aspect, exposing in steps (a) and (b) induces apoptosis in the one or more cells. Disrupting preferably results in cell death and/or cell ablation. Preferably, cells disrupted in the body of an organism are removed from the body of the organism. For example, removal of cells can be effected by immune response cells. In one aspect, therefore, the method comprises administering to the organism an agent which modulates an immune response.

In a further aspect, the method comprises the step of exposing the one or more target cells to an agent for facilitating cell death. The cell-death facilitating agent can be selected from the group consisting of an oligonucleotide, a ribozyme, an antibody, and enzyme, a cytotoxic agent, a cytostatic agent, a cytokine, GM-CSF, IL-2, an immunogen, and combinations thereof.

The invention also provides a system for disrupting a cell. The system comprises an electrosensitisation module comprising an electrical field generator for sensitising a cell to render it susceptible to disruption by an energy source, thereby to produce a sensitised cell, and an ultrasound generating module in communication with the electrosensitisation module for delivering ultrasound energy to said sensitised cell at a level sufficient to disrupt said cell. Either module can be provided separately, or as integrated but removable units, or as integrated but non-removable units. When the modules are part of an integrated system, they can be placed in fluid communication with each other such that cells can move from one module to another.

Preferably, the electric field generator delivers an electric field at a sufficient energy level and for a sufficient amount of time such that the sensitised cell is rendered more susceptible to disruption by ultrasound than an unsensitised cell. Preferably, the electric field generator can generate an electric field from 1 Volt/cm to 10 kVolts/cm in vivo. In one aspect, the ultrasound generating module is capable of generating ultrasound at a power level of from 0.05 W/cm$^2$ to 100 W/cm$^2$.

In another aspect, the electrosensitisation module comprises a housing having a lumen and the ultrasound module is positioned within the lumen. The ultrasound module can be removable from said electrosensitisation module. In a further aspect, the system comprises an insulation ring comprising a material which absorbs ultrasound and which insulates the electric field generator from short circuit discharge.

Preferably, the electric field generator comprises one or more electrodes. In one aspect, the electrodes are in the form of an array of needles. In another aspect, the electrosensitisation module comprises a delivery element comprising a housing defining a lumen through which fluids (e.g., cell-death facilitating agents, therapeutic agents, and the like) can be delivered to a target site.

Preferably, the system is in communication with a power source. More preferably, the system is in communication with a processor which can be programmed to implement operating parameters for the system.

The invention also provides a medical access device comprising a housing defining a lumen and wherein the system described above is positioned within the lumen. Preferably, the system is removable from the medical access device. The medical access device can comprise one or more of an irrigation source, irrigation channels, an optical system for transmitting light to and receiving light from a target site, or a cutting element. In one aspect, the medical access device is selected from the group consisting of a catheter, an endoscope, and a laparoscope.

The invention further provides an electrosensitisation module comprising a housing defining a lumen and an electric field generator in communication with the lumen which is suitable for generating an electric field within the lumen which is not of sufficient strength to electroporate a cell placed within the lumen, but is of sufficient strength to sensitise a cell so that it is more sensitive to disruption than a non-sensitised cell.

The invention also provides a method of inducing apoptosis in a cell. The method comprises exposing the cell to an electric field and exposing the cell to ultrasound.

In another aspect, the invention provides a method of identifying a gene product which is involved in an apoptotic process. The method comprises the steps of: inducing apoptosis in a cell by exposing the cell to an electric field and ultrasound and detecting a gene product whose expression changes in response to the exposing. The expression of the gene product can be induced, up-regulated, or down-regulated. In a further aspect, the method comprises the steps of altering the expression of a gene product or a gene encoding the gene product in a cell, exposing the cell to an electric field, exposing the cell to ultrasound, and measuring apoptosis. Apoptosis can be measured by detecting the presence or absence of fragmented DNA in a sample of nucleic acids from the cell. Apoptosis also can be measured by observing morphological features of the cell, by measuring the amount of histone complexes comprising fragmented DNA in a sample, by measuring the activity or determining the presence of proteases characteristically involved in apoptotic processes (e.g., such as caspase 3), or by other assays routinely performed in the art.

In one aspect, the invention provides a method of identifying a molecule which affects apoptosis of a cell. The method comprises the steps of: contacting a cell with a candidate molecule, exposing the cell to an electric field, exposing the cell to ultrasound and determining whether apoptosis is affected as a result of the contacting. In one aspect, the step of determining comprises measuring the expression of one or more genes involved in an apoptotic pathway. This measuring can comprise measuring one or more of: the amount, localisation, or function of gene product(s) of the one or more genes. In one embodiment, the step of determining comprises detecting the fragmentation of DNA in the cell.

The invention also provides a gene or gene product or a molecule identified according to the methods described above.

BRIEF DESCRIPTION OF THE FIGURES

The objects and features of the invention can be better understood with reference to the following detailed description and accompanying drawings.

DETAILED DESCRIPTION OF THE INVENTION

Figure 1:
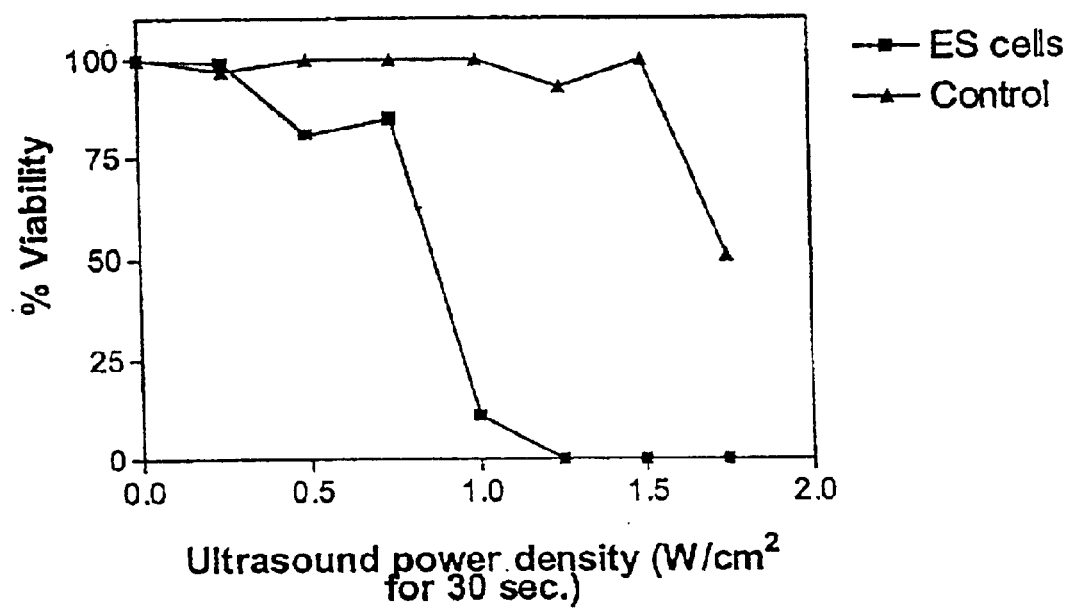
FIG. 1 is a graph illustrating the effect of ultrasound on control (▲) and electro-sensitised (■) 707 cells in suspension according to one embodiment of the invention. Cells were electrosensitised by exposure to electric pulses of 3.625 kV/cm at 1 $\mu$F and cell viability was determined immediately following treatment with ultrasound.

The invention provides a method for selective cell disruption which can be used to ablate and/or remove unwanted cells from the body of an organism. In one aspect, the method involves sensitising cells to a disrupting stimulus such that the cells can be disrupted using frequencies and energies of a disrupting stimulus that are insufficient to cause disruption of unsensitised cells. Preferably, the cells are sensitised by exposure to sensitising stimulus such as an electric field or one or more electric pulses. Preferably, the disrupting stimulus is ultrasound. The combination of sensitisation and disruption results in the selective cell death, cell ablation or cell killing of one or more target cells at a target site comprising a plurality of cells. In one aspect, cell death occurs because of the induction of apoptosis in sensitised, disrupted cell.

The methods, devices, products, etc., described herein will employ, unless otherwise indicated, conventional techniques of chemistry, molecular biology, microbiology, recombinant DNA and immunology, which are within the capabilities of a person of ordinary skill in the art. Such techniques are explained in the literature. See, for example, Sambrook, et al., 1989, In *Molecular Cloning: A Laboratory Manual,* Second Edition, Books 1–3, Cold Spring Harbor Laboratory Press; Ausubel et al., 1995, and periodic supplements, In *Current Protocols in Molecular Biology,* ch. 9, 13, and 16, John Wiley & Sons, New York, N.Y.; Roe et al., 1996, In *DNA Isolation and Sequencing: Essential Techniques,* John Wiley & Sons; Polak et al., 1990, In *In Situ Hybridization: Principles and Practice;* Oxford University Press; Gait (Editor), 1984, In *Oligonucleotide Synthesis: A Practical Approach,* Irl Press; and. Lilley and Dahlberg, 1992, In *Methods of Enzymology: DNA Structure Part A: Synthesis and Physical Analysis of DNA,* Methods in Enzymology, Academic Press. Each of these general texts is herein incorporated by reference.

Definitions

The following definitions are provided for specific terms which are used in the following written description.

The term "sensitised" is intended to indicate that the cells according to the invention have been treated in order to render them more susceptible to a stimulus than non-sensitized cells. Preferably, at least 70%, at least 75%, at least 80%, at least 90%, at least 95% to about 100% of sensitised cells are killed when exposed to the stimulus while less than 20%, preferably less than 10%, less than 5%, less than 1%, or about 0% non-sensitised cells remain alive. Although the cells are sensitised to the stimulus, sensitisation itself causes substantially no cell death unless preceded by or accompanied by a stimulus, i.e., less than 10%, less than 5%, less than 1% and preferably 0% cells are killed by sensitisation in the absence of a stimulus.

As used herein, "destabilization" refers to an alteration of a membrane of a cell that makes the cell more susceptible to disruption in vitro or in vivo upon exposure to an energy field such as ultrasound. In one embodiment of the invention, a cell which is destabilized is a cell which is disrupted when less than 20%, and preferably less than 10%, less than 5%, or less than 1% of non-sensitised cells are disrupted. Destabilisation may be achieved by exposing a cell to an energy field, such as an electric field.

As used herein, "disrupt" signifies that the target tissue and/or the cells thereof is or are damaged, for example by lysis, necrosis, apoptosis, etc., such that the cells are either killed outright or recognised as damaged by the internal defence systems of the organism and eliminated thereby. A tissue or cell is "ablated" when sufficient damage takes place that it is eliminated from the body of the organism.

As used herein, "cell disruption" refers to a process in which the intracellular components of a cell are released extracellularly, i.e., the cell is at least partially lysed and can no longer carry out its normal metabolic functions. A disrupted cell is either killed outright or recognised as damaged by the internal defence systems of an organism and eliminated thereby. In a preferred embodiment, a disrupted cell is one which has subdivided into one or more apoptotic bodies.

The term "electrosensitisation" as used herein refers to the sensitisation of a cell that occurs upon momentary exposure of the cell to one or more pulses of a high electric field. Electrosensitisation typically involves the use of electric fields which do not possess sufficient energy to electroporate cells. Electroporation, which facilitates the passage of agents into a cell without significant loss of cellular contents or cell viability is well known in the art, and apart from the energy levels involved, is similar to electrosensitisation. Cells which are electroporated may become electrosensitised. However, as the term is used in the instant application, electrosensitisation is carried out at energy levels insufficient to electroporate a cell and permit the passage of substances through the cell membrane (e.g., less than 10%, and preferably, less than 1% of an agent in a solution to which the cell is exposed during electrosensitisation would be able to enter the cell).

As used herein, the term "electric pulse" includes one or more pulses at variable capacitance and voltage and including exponential and/or square wave and/or modulated wave forms.

As used herein, "electric field energy" is the electrical energy to which a cell is exposed during an electrosensitisation procedure as described herein.

As used herein, the term "ultrasound" refers to a form of energy which consists of mechanical vibrations the frequencies of which are so high they are above the range of human hearing.

The term "target" refers to the site to which a stimulus (e.g., an electric pulse or ultrasound energy) or agent is being directed to, to achieve a therapeutic effect. As used herein, a "target" refers to any of: a cell, a group of cells, a tissue, a portion of an organ, a portion of a tumor, an entire tumor, and the like.

As used herein, the term "agent" includes, but is not limited to, an atom or molecule, inorganic or organic, which is a biological effector molecule or which encodes a biological effector molecule, and/or which is a diagnostic molecule whose presence within a cell can be detected.

As used herein, the term "biological effector molecule" or "biologically active molecule" refers to an agent that has activity in a biological system.

As used herein, an "imaging agent" or a "diagnostic molecule" is an agent which may be detected, whether in vitro or in vivo in the context of a tissue, organ or organism in which the agent or molecule is located.

As used herein, the term "nucleic acid" is defined to encompass DNA and RNA or both synthetic and natural origin which DNA or RNA may contain modified or unmodified deoxy- or dideoxy-nucleotides or ribonucleotides or analogues thereof. The nucleic acid may exist as single- or double-stranded DNA or RNA, an RNA/DNA heteroduplex or an RNA/DNA copolymer, wherein the term "copolymer" refers to a single nucleic acid strand that comprises both ribonucleotides and deoxyribonucleotides.

The term "synthetic," as used herein, is defined as that which is produced by in vitro chemical or enzymatic synthesis.

As used herein, the term "agent-MTS conjugate" refers to an agent which is coupled to a membrane translocation sequence or "MTS". Coupling may be permanent or transient and may involve covalent or non-covalent interactions (including ionic interactions, hydrophobic forces, Van der Waals interactions, etc). The exact mode of coupling is not important, so long as the membrane translocation sequence is effective in allowing the agent to cross the cell membrane of a target cell. Accordingly, where reference is made to "comprising," "conjugation," "coupling," "joining", etc., these references should be taken to include any form of interaction between the agent to be delivered and the membrane translocation sequence, in such a manner as to allow intracellular delivery of the agent. This term also includes fusion proteins comprising an MTS sequence and a polypeptide agent to be delivered. In some embodiments, the MTS sequence may further comprises a nuclear localisation sequence or a localisation sequence which further directs the agent into a specific subcellular compartment.

As used here, the term 'translocation' refers to transfer of an agent across a membrane such that the agent is internalised within a cell.

As used herein, the term "fragment of an MTS sequence" or a "sub-sequence of an MTS sequence" refers to a polypeptide or peptide (or nucleic acid encoding the same) which comprises the biological activity of the MTS sequence, i.e., retains the ability to translocate an agent to which it is coupled across a cell and/or nuclear membrane or retains the ability to encode a polypeptide or peptide which can translocate an agent across a cell and/or nuclear membrane.

The term "variant of an MTS sequence" or a "mutated MTS sequence" refers to an MTS with one or more amino acid substitutions, deletions or insertions, or a nucleic acid sequence encoding an MTS with one or more substitutions, deletions or insertions which nevertheless retains MTS activity, i.e., the ability to translocate an agent to which it is coupled into a specific subcellular compartment.

The term "homolog of an MTS sequence" refers to a sequence which has at least 60% percent of its amino acid residues identical with the residues in a reference MTS sequence after aligning the two sequences and introducing gaps, if necessary, to achieve the maximum percent homology, using any computer program which is known in the art for performing the comparison, e.g., such as the GCG software package (available at http://www.gcg.com), the GAP program in the GCG software package (available at http://www.gcg.com), the NBLAST and XBLAST programs (version 2.0) of Altschul, et al. (1990) J. Mol. Biol. 215:403–10, or the Gapped BLAST program of Altschul et al., (1997) Nucleic Acids Res. 25(17):3389–340 (the entireties of these references are incorporated herein by reference). In a preferred embodiment, a homolog is at least 70% identical, at least 80% identical, or at least 90% identical, to a reference MTS sequence. A "homolog of an MTS sequence" as used herein has the ability to translocate an agent to which it is conjugated across a cell membrane.

As used herein the term "introducing" includes but is not limited to the administration of delivery vehicle and/or an agent into a vertebrate. As used herein in reference to administration of an agent to a vertebrate, the term "introducing" includes but is not limited to causing the agent to enter the circulatory system of the vertebrate by transfusion or to infusing an agent to a target site.

As defined herein, a "modified nucleic acid," or "modified oligonucleotide" refers to nucleic acids and oligonucleotides that contain non-naturally occurring nucleotides, and can be modified at one or more of the sugars, bases, or internucleotide linkages of a nucleic acid.

"Nanoparticles" are defined as solid colloidal particles ranging in size from about 10 nm to 1000 nm.

As used herein, the term "more", and other terms of degree or comparison to a baseline (e.g., reducing, inhibiting, enhancing, slowing, and the like) refer to statistically significant differences observed at confidence levels of at least 95%. For example, sensitised cells "more susceptible to a disrupting stimulus than non-sensitised cells" indicates that the sensitised cells are disrupted when less than 20%, preferably less than 10%, and more preferably, less than 1% of cells which are not sensitised are disrupted.

As used herein, "destabilization" refers to an alteration of a membrane of a cell that makes the cell more susceptible to disruption in vitro or in vivo upon exposure to an energy field such as ultrasound. In one embodiment of the invention, a cell which is destabilized is a cell which is disrupted when less than 20%, and preferably less than 0.5%–10%, or less than 1% of non-sensitised cells are disrupted. Destabilisation may be achieved by exposing a cell to an energy field, such as an electric field.

As used herein, the term "electric field" includes one or more pulses at variable capacitance and voltage and including exponential and/or square wave and/or modulated wave and/or modulated square wave forms.

The term "electrosensitisation" as used herein refers to the sensitisation of a cell that occurs upon momentary exposure of the cell to one or more pulses of an electric field. Electrosensitisation typically involves the use of electric fields which do not possess sufficient energy to electroporate cells (e.g., less than 1% of an agent can enter the cell). "Electroporation" also involves exposing cells to electric fields and cells which are electroporated can become electrosensitised. However, electroporation alters the permeability of cell membranes to facilitate the passage of agents into cells without significant loss of cellular contents or cell viability and as used herein, electrosensitisation is carried out at energy levels insufficient to electroporate a cell.

As used herein, the term "electric pulse" includes one or more pulses at variable capacitance and voltage and including exponential and/or square wave and/or modulated wave forms.

As used herein, the term "ultrasound" refers to a form of energy which consists of mechanical vibrations, the frequencies of which are so high they are above the range of human hearing.

The term "target" refers to the site to which a stimulus (e.g., an electric pulse or ultrasound energy) or agent is being directed to, to achieve a therapeutic effect. As used herein, a "target" refers to any of: a cell, a group of cells, a portion of a tissue, a tissue, a portion of an organ, a portion of a tumor, an entire tumor, and the like.

As used herein, the term "agent" includes, but is not limited to, an atom or molecule, inorganic or organic, which is a biological effector molecule or which encodes a biological effector molecule. An agent can additionally be a diagnostic molecule whose presence within a cell can be detected.

As used herein, the term "biological effector molecule" or "biologically active molecule" refers to an agent that has activity in a biological system.

As used herein, an "imaging agent" or a "diagnostic molecule" is an agent which may be detected, whether in vitro or in vivo in the context of a tissue, organ or organism in which the agent or molecule is located.

As used herein, the term "agent-MTS conjugate" refers to an agent which is coupled to a membrane translocation sequence or "MTS". Coupling may be permanent or transient and may involve covalent or non-covalent interactions (including ionic interactions, hydrophobic forces, Van der Waals interactions, etc). The exact mode of coupling is not important, so long as the membrane translocation sequence is effective in allowing the agent to cross the cell membrane of a target cell. Accordingly, where reference is made to "comprising," "conjugation," "coupling," "joining" etc, these references should be taken to include any form of interaction between the agent to be delivered and the membrane translocation sequence, in such a manner as to allow intracellular delivery of the agent. This term also includes fusion proteins comprising a membrane translocation sequence and a polypeptide agent to be delivered. In some embodiments, the MTS sequence may further comprises a nuclear localization sequence or a localization sequence which further directs the agent into a specific subcellular compartment.

As used here, the term "translocation" refers to transfer of an agent across a membrane such that the agent is internalized within a cell.

As defined herein, a "modified nucleic acid," or "modified oligonucleotide" refers to nucleic acids and oligonucleotides that contain non-naturally occurring nucleotides (e.g., nucleotides with modified sugars, bases, and/or internucleotide linkages).

As defined herein, an "analog" of a nucleotide refers a nucleotide comprising one or more substituted atoms wherein the substituted atoms have similar biological properties as (i.e., properties not statistically significantly different from) the atoms which are replaced.

As defined herein, a "fragment" of a protein or nucleic acid sequence is subsequence of a protein or nucleic acid which still retains the biological activity of the protein or nucleic acid. For example, a fragment of a protein is one which retains the ability to bind or be bound by receptors and/or ligands, or which retains a catalytic site, in the case of an enzyme. In the case of a nucleic acid, a fragment is one which retains the ability to hybridize specifically to a transcript comprising the nucleic acid or to a chromosome or vector which comprises the nucleic acid.

As used herein the term "introducing" includes, but is not limited to, the administration of delivery vehicle and/or an agent into a vertebrate. As used herein in reference to administration of an agent to a vertebrate, the term "introducing" includes, but is not limited to, causing the agent to enter the circulatory system of the vertebrate by transfusion or by infusing an agent to a target site.

As used herein, the term "in situ" refers to applying a stimulus (e.g., electrosensitisation and/or ultrasound) at the site of the target in an organism, without having to remove the target from the organism.

As used herein, "cell death" refers to a process which prevents a cell from carrying out its normal metabolic functions. Cell death encompasses both apoptosis and necrosis.

As used herein, "ablation of a target" refers to the removal of a target from a body (e.g., wherein disrupted cells are removed from their situs by such processes as macrophage ingestion or transport through the circulation).

An agent which is "facilitating cell death" or a "cell-death facilitating agent" is one which, when exposed to a target (e.g., a cell, tissue, or tissue mass), significantly enhances the cell killing ability of treatment with electric field/ultrasound administration (e.g., as determined using routine statistical testing to within 95% confidence levels). Preferably, a agent which facilitates cell death is one which causes a 2-fold or greater increase in cell death as measured by observing disruption of the cell (e.g., microscopically or by measuring apoptosis), and preferably, a ten-fold or greater increase.

"Cytotoxicity" refers to the cell killing property of a chemical compound (e.g., such as a food, cosmetic, or pharmaceutical) or a mediator cell (e.g., cytotoxic T cell). In contrast to the terms "necrosis" and "apoptosis" (discussed in separate sections below), the term cytotoxicity need not necessarily indicate a specific cellular death mechanism. For example, cell mediated cytotoxicity (that is, cell death mediated by either cytotoxic T lymphocytes [CTL] or natural killer [NK] cells) combines some aspects of both necrosis and apoptosis. The terms "cytotoxic" and "cytoxic drug" or "cytotoxic agent" are used interchangeably, and refer to any of a group of molecules that are toxic to cells and cause cell death or prevent any cell process such as cell growth, proliferation, or replication. The latter are also referred to as "cytostats" or "cytostatic agents".

As used herein, exposure to an electric field "under in vivo conditions" refers to an electric field to which a cell is exposed in situ. Similarly, exposure to an electric field "under in vitro conditions." refers to an electric field to which a cell is exposed outside of the body, for example, in an electroporation cuvette.

As used herein, "detecting a gene product whose expression changes" refers to detecting at least a two-fold, and preferably, at least a five-fold, or at least a ten-fold increase or decrease in the level or activity of a gene product (e.g., an mRNA or protein). The "level" of a gene product refers to a detectable amount. For example, in the case of an mRNA, at least a two-fold level change in the amount of mRNA as determined using a hybridization-based assay (e.g., a Northern, or RT-PCR assay, and the like) must be observed to constitute a "change" in expression. In the case of a protein, at least a two-fold change in the amount of protein must be observed in an immunoassay, or other assay based on the affinity of the protein for a binding partner (e.g., such as an antibody or a receptor). A "change in the activity" of protein refers to an at least two-fold increase in the activity of the protein. For example, a "change in the activity" of an enzyme refers to an at least two-fold increase or decrease in the catalytic activity of the enzyme as measured by an amount of product formed or substrate consumed. As "change in activity" can also refer to in at least two-fold increase or decrease in the binding affinity of a protein for a binding partner (e.g., a ligand for its receptor, and vice versa). A change in the activity of a transcription factor refers to an at least two-fold change in the amount of mRNA produced whose expression is regulated by binding of the transcription factor to a regulatory element (e.g., a promoter or enhancer) upstream of the gene which transcribes the mRNA. In some cases, a change in expression, refers to a change in the localization of a protein or mRNA which is observed in at least 5%, and preferably at least 10% of cells in a population of cells being monitored (e.g., observed under a microscope).

As used herein, the term, an electrosensitisation module "in communication with" with an ultrasound generating module refers to an embodiment where a cell which is in sufficient proximity to an electric field generator to be exposed to an electric field when the generator is activated is also in sufficient proximity to an ultrasound generator to be exposed to ultrasound when the ultrasound generator is activated. Preferably, the electrosensitsation module defines a lumen in which the ultrasound generator is positioned. However, in some applications, such as in vitro or ex vivo applications, the electrosensitisation module and the ultrasound module are connected to each other by a reversibly sealable connecting element, and a cell is transported from one module to another (e.g., such as by diffusion through a medium when the connecting element is not sealed, or by application of a force, such as pressure or gravity on the medium in the electrosensitisation module which forces the medium into the ultrasound module when the connecting element is not sealed).

Cell Ablation

The general mechanism of disruption or ablation of cells according to the invention comprises two steps: a sensitisation step followed by a disruption step. In general, sensitisation and disruption are achieved by exposure of cells to a stimulus such as one or more energy sources, including particles, waves or fields. Preferably, the cells are nucleated cells.

In one aspect, a nucleated cell is rendered susceptible to disruption by a stimulus by sensitisation such that disruption is achieved by exposure of a sensitised cell to a stimulus at a frequency and/or energy sufficient to disrupt sensitised but does not substantially disrupt unsensitised cells. Preferably, the sensitising stimulus and disrupting stimulus are not the same.

In one aspect, cells are "electrosensitised" by exposure to an electric field and disrupted by exposure to ultrasound. Exposure to an electric field can occur before, during, or after exposure to ultrasound. When it occurs after exposure to ultrasound, ultrasound may be considered the sensitising stimulus and exposure to the electric field may be considered the disrupting stimulus. Generally, the stimulus most proximate in time to cell disruption is considered the disrupting stimulus. The step of sensitisation provides for the selectivity of the method. The level of a disrupting stimulus, which disrupts a sensitised cell preferably, will have substantially no effect on a non-sensitised, i.e., non-target cell. In addition to ultrasound, disruption stimuli also can include laser light and other energy sources.

In a preferred aspect, exposure to ultrasound and electric field energy (in any order) results in cell death, cell ablation, or cell killing. Most preferably, cell death, cell ablation, or cell killing, results from apoptosis of the exposed cell.

The invention is applicable to any multicellular organism, and is advantageously applied to organisms having distinct tissues which may be targeted for electrosensitisation. Advantageously, the organism is a mammal. Preferably, the target for disruption is a tumor tissue, more preferably a solid tumor tissue. Most preferably, a target (e.g., cell, tissue or tumor, etc.) is treated in situ in the organism.

Preferably, the target is a cell which is part of a tissue mass in the organism and a proportion of the tissue is electrosensitised which comprises the cell. The proportion of the tissue which is electrosensitised will vary, but advantageously, substantially all of the tissue becomes electrosensitised. For example, about 50%, 60%, 70%, 80%, 90% or 100% of the cells of the tissue can be electrosensitised. The target cell is preferably a nucleated cell and can comprise a nerve cell, muscle cell, epidermal cell, blood vessel cell (e.g., a capillary cell), an epithelial cell, an endothelial cell, and the like. The cell can be normal, diseased, infected, cancerous, or otherwise abnormal.

Preferably, a target cell is disrupted which is an abnormally proliferating cell, e.g., a benign tumor or malignant tumor. The cell can be in a tissue or tissue mass (e.g., such as a cyst or tumor) and the method can be used instead of, or to complement, traditional cancer therapies such as chemotherapy, radiotherapy or surgery. For example, benign tumors may be selectively ablated using the methods according to the invention where methods such as chemotherapy and radiotherapy would otherwise be contraindicated.

Preferably, where the tissue comprises a tumor, treatment of the tissue leads to partial or complete remission. In a particular embodiment, treatment leads to no significant cell growth of tumor cells at the treated site, and preferably, throughout the organism, within a relevant period. Such a period is preferably 1 day, 1 week, 1 month, 2, 3, 4, 5, or 6 months, or even longer, for example, a year, two years, five years, ten years, 20 years, etc.

Electric field energy is preferably administered substantially as described in the art, using one or more electric pulses of from about 1 Volt/cm to about 10 kVolts/cm under in vivo conditions. The electric pulse may be applied for between 1 $\mu$s and 100 milliseconds.

Ultrasound is advantageously administered at a power level of from about 0.05 W/cm$^2$ to about 100 W/cm$^2$. Diagnostic or therapeutic ultrasound may be used, or combinations thereof.

Single or multiple applications of an electric field, as well as single or multiple applications of ultrasound are also possible, in any order and in any combination. In one aspect, multiple cycles of sensitisation followed by disruption are used (i.e., S+D, S+D, S+D . . . ). For example, the method can follow the sequence ES+US, ES+US, ES+US . . . (where ES is electrosensitisation and US is ultrasound). Two or more applications of sensitisation also may be followed by a single disruption cycle (i.e., S+S . . . +D). Further, two or more applications of an electric field may be followed by a single application of ultrasound (i.e., ES+ES . . . +US), or vice versa (i.e., US+ES+ES . . . ). A single electrosensitising field may be applied, followed by two or more ultrasound applications (e.g., ES+US+US . . . ) and vice versa (i.e., US+US+ES . . . ). Multiple electrosensitising fields also may be applied followed by multiple ultrasound applications (ES+ES . . . +US+US . . . ), or multiple ultrasound applications by multiple electrosensitising fields (US+US . . . +ES+ES . . . ). In each of the above scenarios, the ultrasound and/or the electric field may be delivered as single or multiple continuous applications, or as pulses (pulsatile delivery). It should also be obvious to those of skill in the art that combinations of the above sequences also can be used.

Sensitisation

According to a general aspect, cells are sensitised to render them more susceptible to disruption by a stimulus than unsensitised cells. Such cells are capable of being selectively disrupted at a target site by exposure to a stimulus. For example, sensitisation may be achieved by exposing the cells to ultrasound. Preferably, such ultrasound-sensitised cells are capable of being disrupted by subsequent exposure to an electric field. This aspect is exemplified in Example 7.

As discussed above, a preferred means of sensitisation is electrosensitisation. Electrosensitisation is described in WO 01/07011, and is described in detail below.

According to this method, a momentary exposure of a cell to one or more pulses at high electric field strength results in membrane destabilisation. The strength of the electric field is adjusted up or down depending upon the resilience or fragility of cells in the targeted tissue.

Preferably, the electric field has a strength of from about 1 V/cm to about 10 kV/cm under in vitro conditions, more preferably from about 0.5 kV/cm to about 4.0 kV/cm under in vitro conditions. Preferably the electric field has a strength of from about 1 V/cm to about 10 kV/cm under in vivo conditions (see, WO 97/49450). However, the electric field strength maybe lowered where the number of pulses delivered to the target site are increased. Thus, pulsatile delivery of electric fields at lower field strengths is also encompassed within the scope of the invention. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Electrosensitisation may be performed in a manner substantially identical to the procedure followed for electroporation, with the exception that the electric field is delivered in the absence of an exogenous agent of interest, as set forth below, and may be carried out at different electric field strengths (and other parameters) from those required for electroporation. For example, lower field strengths may be used for electrosensitisation.

In known electroporation applications, the electric field comprises a single square wave pulse on the order of 1000 V/cm, of about 100 µs duration and is sufficient to cause the membranes of cells exposed to the electric field to become porous, allowing entry of agents (e.g., nucleic acids) into cells. In contrast, the electrosensitisation used herein to sensitise cells to disruption generally employs an electric field strength which is insufficient to allow any substantial entry of agents into a cell (e.g., less than 10%, less than 5%, and preferably, less than 1% of an agent would be able to enter the cell). Preferably, electric field strengths of from about 1 V/cm to about 10 kV/cm, and more preferably, from about 0.5 kV/cm to about 4.0 kV/cm (see, e.g., WO 97/49450) are used to electrosensitise a cell. In one aspect, pulsatile delivery of electric fields to a target site is used to lower electric field strengths even more. Multiple pulses such as double pulses of the same strength and capacitance or sequential pulses of varying strength and/or capacitance can be used. Preferably, an electric pulse is delivered as a waveform selected from an exponential waveform, a square waveform, a modulated waveform and a modulated square waveform.

Preferably, the sensitisation procedure is carried out in the absence of foreign material, for example, material intended for incorporation into the cell. Thus, for example, where electrosensitisation is followed by application of ultrasound, the electrosensitisation procedure is carried out in the absence of foreign material, for example, material intended for incorporation into the cell. However, and as described in further detail below, other agents (such as cytotoxics and cytokines), may be applied to the cells after administration of the sensitiser (e.g., at least 30 seconds, at least 1 minute, at least 2 minutes, or at least 5 minutes after exposure to an electric field) and/or after administration of the disruption means (e.g., ultrasound) to promote cell death. Such cell-death facilitating agents may be administered to prior to the disruption stimulus (e.g., ultrasound), i.e., to sensitised cells. Furthermore, they may be applied together with, or subsequent to, administration of the disruption stimulus. However, unlike methods for in vivo electroporation of the prior art, the present invention is not primarily concerned with the modification of cell membranes as a result of electrical field energy in order to facilitate the loading of pharmaceuticals or other agents into the cell.

When electric fields are used as disrupting stimuli, generally the same parameters may be used as described above.

Ultrasound

According to the present invention, cells which have been sensitised (in particular, electrosensitised) may be disrupted by the application of ultrasound directed at a target tissue and/or cell.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From *Ultrasonics in Clinical Diagnosis*, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound typically is used in an energy density range of up to about 100 mW/cm$^2$ (FDA recommendation), although energy densities of up to 750 mW/cm$^2$ have been used. In physiotherapy, ultrasound is typically used as an energy source in a range up to about 3 to 4 W/cm$^2$ (WHO recommendation). In other therapeutic applications, higher intensities of ultrasound may be employed, for example, HIFU at 100 W/cm$^2$ up to 1 kW/cm$^2$ (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136–142. Another form of focused ultrasound is high intensity focused ultrasound (HIFU) which is reviewed by Moussatov et al., 1998, *Ultrasonics* 36(8): 893–900 and TranHuuHue et al., 1997, *Acustica*, 83(6): 1103–1106.

Preferably, a combination of diagnostic ultrasound and a therapeutic ultrasound is employed. This combination is not intended to be limiting, however, and the skilled artisan will appreciate that any variety of combinations of ultrasound may be used. Additionally, the energy density, frequency of ultrasound, and period of exposure may be varied. What is important is that the application of ultrasound is able to disrupt the sensitised target cells.

Preferably, the ultrasound is applied to target tissue with sufficient strength to disrupt sensitised cells but without damaging the surrounding tissues, such that less than 10%, preferably, less than 5%, and more preferably, less than 1% of cells within surrounding tissues are disrupted.

Preferably, the exposure to an ultrasound energy source is at a power density of from about 0.05 to about 100 Wcm$^{-2}$.

Even more preferably, the exposure to an ultrasound energy source is at a power density of from about 1 to about 15 $Wcm^{-2}$.

Preferably, the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, a target is exposed to an ultrasound energy source at an acoustic power density of from about 0.05 $Wcm^{-2}$ to about 10 $Wcm^{-2}$ with a frequency ranging from about 0.015 to about 10 MHz (see, WO 98/52609). However, alternatives are also possible, for example, exposure to an ultrasound energy source at an acoustic power density of above 100 $Wcm^{-2}$, but for reduced periods of time, for example, 1000 $Wcm^{-2}$ for periods in the millisecond range or less.

The ultrasound may be applied either continuously, or in the form of pulses. Thus, the ultrasound may be continuous wave ultrasound or pulsed wave ultrasound. In a highly preferred embodiment, the ultrasound is applied at a power density of 0.7 $Wcm^{-2}$ or 1.25 $Wcm^{-2}$ as a continuous wave. Higher power densities may be employed if pulsed wave ultrasound is used. Preferably the application of the ultrasound is in the form of multiple pulses; thus, both continuous wave and pulsed wave (pulsatile delivery of ultrasound) may be employed.

Use of ultrasound, like light, can be focused very accurately on a target. However, ultrasound can be focussed more deeply into tissues than light. It is therefore better suited to penetration of whole tissue (including, but not limited to, a lobe of the liver) or whole organ (including, but not limited to, the entire liver) or an entire muscle (e.g., such as the heart). Another important advantage is that ultrasound is a non-invasive stimulus which is used in a wide variety of diagnostic and therapeutic applications and is therefore familiar to health care workers. By way of example, ultrasound is well known in medical imaging techniques and, additionally, in orthopaedic therapy. Furthermore, instruments suitable for the application of ultrasound to a subject vertebrate are widely available and their use is well known in the art. See, e.g., as described in U.S. Pat. No. 5,112,300; U.S. Pat. No. 5,180,363; U.S. Pat. No. 4,989,583; U.S. Pat. No. 4,931,047; U.S. Pat. No. 4,922,902; and U.S. Pat. No. 3,805,787; the entireties of which are incorporated by reference herein.

Low Intensity Sensitisation and Disruption

As noted above, low intensity electric fields may be employed to sensitise cells. Low voltage strengths may be set up using alternating current or, preferably, using direct current (DC). Such cells also may be disrupted with low intensity ultrasound.

Treatment of tumors with low voltage/current direct current (DC) without application of ultrasound ("electrochemical treatment") has been described in Nordenstrom, 1989, *Am. J. Clin. Oncol.* 12: 530–536 and Wojcicki et al., 2000, *Med. Sci. Monit.* 6: 498–502. However, in all cases, both in the clinic and in animal models it has been found that such treatment leads to the formation of necrotic lesions and in many cases the target tissues re-establish at the treatment site. The low voltage electrosensitisation described here, however, when combined with ultrasound, can decrease the probability of tumor remission while simultaneously decreasing the formation of necrotic lesions.

Treatment with low intensity electric fields, preferably coupled with low intensity ultrasound also may be employed for the treatment of benign disorders. Benign disorders which may be treated include any disorder which may be cured, treated or ameliorated by cell or tissue disruption or excision. For example, low intensity ultrasound and/or electric fields may be used to treat skin conditions such as warts, papillomas, psoriasis, eczema, moles, etc. In addition, therapies employing this aspect can be used to accomplish drug- and surgery-free treatment of benign disorders such as benign breast and prostate disease, human papilloma virus (HPV) infection (condylomata acuminata, Longstaff and von Krogh, 2001, *Reg. Tox. Pharm.* 33: 117–137), eradicating benign granulomatous tissues remaining after localised infections (Hildebrandt et al., 1998, *Strahlenther Onkol.* 174: 580–588).

Lipomas, which are fatty deposits, as well as other conditions involving deposits of excess fat, also may be treated. For example, the methods according to the invention may be used to destroy or disrupt adipose cells or tissue as a substitute for cosmetic treatments such as liposuction.

The methods according to the invention are also suitable for treatment of relatively large areas or parts of the body, particularly for removal of large areas of adipose tissues for cosmetic purposes. In general, the methods can be used to remove any types of unwanted cells for therapeutic or cosmetic purposes.

Thus, in a particular embodiment, direct current at low voltage is used to electrosensitise cells. Electric field strengths as low as from 1 V/cm, preferably 5 V/cm to 100 V/cm more, preferably between 10 V/cm and 20 V/cm, e.g., 10, 11, 12, 13, 14, 15, 16, 17, 18, 19 or 20V/cm may be employed. Electric field strengths also may be measured in terms of current; preferably, the current applied is between 100 $\mu$A to 200 mA, preferably between 1 mA and 10 mA.

Where low intensity fields and/or direct current is used, the time of exposure of the cells to the field may typically be in the order of seconds to minutes. Thus, the cells may be exposed to the electric field for more than 100 $\mu$s, for example, 1 millisecond or more, preferably 0.5 seconds or more. Most preferably, the cells are exposed for more than 1 second, preferably, 5, 10, 30, 60, 120, 180, 240, 300 or more seconds. The cells may be exposed for 1, 2, 3, 4, 5, 6, 7, 8, 9, 10, 15, 20, 25, 30 or more minutes.

The characteristics of the electric field may be constant or vary over the course of exposure, for example, the strength and/or direction of the electric field may be varied. The electric field strength may be steady during the exposure, or may vary in intensity. For example, where the cell is exposed to the field under a constant current setting of the device applying the field, the electric field strength may vary. Thus, for example, where a 5 mA constant current is being applied, the electric field strength may vary between 10 V/cm and 20 V/cm.

In a highly preferred embodiment, the electric field is applied continuously to a target at a field strength of between 10 V/cm and 20 V/cm. The electric field is applied preferably for a period of 100 milliseconds or more, preferably 15 minutes or more.

Cells treated with low electric field strengths, for example, using DC, may be disrupted using ultrasound or other stimulus. Such electrosensitised cells may be disrupted by the use of low intensity ultrasound, e.g., in the diagnostic and/or therapeutic ranges: 100 mW/cm$^2$ up to 750 mW/cm$^2$ or in a range up to about 3 to 4 W/cm$^2$ or more, as described in further detail below. Cells subject to combined treatments employing sensitisation with low electric field strengths are found to undergo cell death by apoptosis.

Agents which Facilitate Cell Death

According to a highly preferred embodiment of this invention, a sensitised target (e.g., cell, tissue or tissue mass, etc.) is exposed to an agent which facilitates cell death. An agent which facilitates cell death is one which, when exposed to a target site enhances cell killing of sensitised, disrupted cells at the target site. Contact with such an agent enhances the cell killing, disruptive or ablation effected by exposure to a sensitising and disrupting stimulus such as an electric field and ultrasound. Furthermore, cell-death facilitating agents may also be used to "mop up" and destroy any cells which have, whether inadvertently or on purpose, been unaffected by the application of the sensitising and disrupting stimulus.

Cell-death facilitating agents may have the ability to promote cell death on their own. Indeed, any agent used for treatment of tumors or cancers as known in the art is a suitable candidate for use as a cell death-facilitating agent in the invention. However, the term "agent which facilitates cell death" and "cell-death facilitating agent" is meant to include those agents which work to promote cell death when used in combination with sensitisation (e.g., electrosensitisation) and exposure to a disrupting stimulus (e.g., ultrasound), as set out above. Preferably, the administration of such cell-death facilitating agents enhances cell killing by more than 10%, more than 20%, more than 30%, more than 40%, more than 50%, more than more than 60%, more than 70%, more than 80%, more than 90%, or more than 100% compared to the cell killing efficiency of sensitising and disrupting stimuli in the absence of a cell-death facilitating agent.

The cell-death-facilitating agent may work in any number of ways. For example, the agent may be directly toxic to the cell. Agents in this category include cytotoxics, which are used in tumor therapy. The agent may be one which causes an immune reaction in the host, to the effect that a target (e.g., cell, tissue, etc.) is eliminated or killed by the patient's normal immune processes (including both cell-mediated and humoral immune responses). Examples of such agents include cytotoxic T cells and dendritic cells. Further, the agent may comprise an agent which is capable of generate or modulate immune responses, such as a cytokine. For example, cytokines such as IL-2, GMCSF, etc., may be used to promote the host's immune response.

The cell-death-facilitating agent need not necessarily be molecular in nature. Thus, the use of treatments which cause cell killing by other means, as known in the art, is also encompassed. Examples include the use of radiation, whether applied externally or internally, to kill cells such as tumor cells. Methods of using radiotherapy as primary or auxiliary therapy for tumors is known in the art.

A target may be exposed to the cell-death-facilitating agent either before, during or after ultrasound treatment. However, in all cases, a sensitising stimulus, such as an electric field which electrosensitises the target is applied substantially prior to administration of the agent (e.g., at least 30 seconds, at least 1 minute, at least 5 minutes, at least 10 minutes, at least 30 minutes). In other words, the sensitising electric field is applied to the target in the absence of such a cell death-facilitating agent. Thus, the cell death-facilitating agent is not primarily responsible for inducing cell disruption or death, but rather, acts in a supplementary role to promote cell death of a sensitised, disrupted target.

The target may be exposed to the cell-death-facilitating agent by any suitable manner. For example, the agent may be topically applied where the target site is skin and the target, such as a skin tumor, comprises epidermal cells. The agent may be systemically administered to the patient or to the system of which the target forms a part. The agent may be administered orally, nasally, delivered using liposome technology, etc. The agent may be directly injected into a mass comprising unwanted cells (such as a tumor mass) or near a mass of unwanted cells (e.g., within 20 cm or less). The agent also can be delivered by delivering a cell expressing the agent at or near the target site. For example, the use of cells to deliver cytotoxic agents is known in the art. See, e.g., as described in Mir et al., *J. Immunotherapy* 17: 30–38, and Orlowski et al., 1998, *Anticancer Drugs* 9: 551–556.

The agent also may be delivered by being loaded into a suitable carrier, such as a red blood cell carrier. Loading and delivery using red blood cells is disclosed in detail in WO 01/07011 and PCT/GB00/03056, the entireties of which are incorporated herein by reference. The agent may be delivered into an intracellular compartment by the use of Membrane Translocation Sequences (MTS), as described further herein. The agent also may be administered in the form of a pharmaceutical composition, as described in further detail below.

Agents useful for use in the present invention are set out below. Preferred agents which are capable of facilitating cell death include cytokines and cytotoxics. These are discussed in further detail elsewhere in this document.

As used herein, the term "agent" includes, but is not limited to, an atom or molecule, wherein a molecule may be inorganic or organic, a biological effector molecule and/or a nucleic acid encoding an agent such as a biological effector molecule, a protein, a polypeptide, a peptide, a nucleic acid, a peptide nucleic acid (PNA), a virus-like particle (e.g., viral capsid or envelope proteins surrounding or presenting an agent), a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid, a fatty acid and a carbohydrate. An agent may be in solution or in suspension (e.g., in crystalline, colloidal or other particulate form). The agent may be in the form of a monomer, dimer, oligomer, etc, or otherwise in a complex. The agent may be coated with one or more molecules, preferably macromolecules, most preferably polymers such as PEG (polyethylene glycol). Use of a PEGylated agent increases the circulating lifetime of the agent once released.

The cell death facilitating agent may be radioactive, i.e., a radionuclide which is used in radiotherapy. The radionuclide may be a radio-isotope as known in the art, for example cobalt-60, iodine-131, etc., or a molecule such as a nucleic acid, polypeptide, or other molecule as explained below conjugated with such a radio-isotope. As noted above, external radiation sources utilising such radionuclides, in the form of external and/or internal radiotherapy may also be used to facilitate cell death at a treated target site.

It will be appreciated that it is not necessary for a single agent to be used, and that it is possible to utilise two or more cell-death facilitating agents, sequentially or simultaneously, to achieve cell death. Accordingly, the term "agent" also includes mixtures, fusions, combinations and conjugates, of atoms, molecules, etc., as disclosed herein. For example, an agent may include but is not limited to: a nucleic acid combined with a polypeptide; two or more polypeptides conjugated to each other; a protein conjugated to a biologically active molecule (which may be a small molecule such as a prodrug); or a combination of a biologically active molecule with an imaging agent.

The biological effector molecule is preferably an immunomodulatory agent or other biological response modifier. In one embodiment, the agent is a biological effector molecule which comprises a nucleic acid selected from the group consisting of an oligonucleotide or modified oligonucleotide, an antisense oligonucleotide or modified antisense oligonucleotide, an aptamer, a cDNA, genomic DNA (including gene sequences or fragments thereof and/or regulatory sequences); RNA, including an mRNA, tRNA, rRNA or a ribozyme (e.g., such as a hammerhead ribozyme as disclosed in Sullivan, 1994, *J. Invest. Dermatol.* 103: 85S–98S and Usman et al., 1996, *Curr. Opin. Struct. Biol.* 6: 527–533, the entireties of which are incorporated by reference herein), or a peptide nucleic acid (PNA), and/or a vector comprising any of the preceding (e.g., such a viral or non-viral DNA or RNA vector, where non-viral vectors include, but are not limited to, plasmids, linear nucleic acid molecules, artificial chromosomes, condensed particles, episomal vectors, and the like).

While in one embodiment, the nucleic acid itself is a biological effector molecule, in another embodiment, the nucleic acid encodes a biological effector molecule which acts as a cell-death-facilitating agent. In this embodiment, the nucleic acid sequence encoding the agent can be operatively linked to transcriptional and translational regulatory elements active in a cell at the target site, suitable for driving the expression of a heterologous gene (see, e.g., as described in Wolff et al., 1990, *Science* 247: 1465–1468;1 U.S. Pat. No. 5,580,859; Sykes et al., 1994, *Human Gene Ther.* 5: 837–844; Vile et al., 1993, *Cancer Res.* 53: 962–967; Hengge et al., 1995, *Nature Genet.* 10: 161–166; Hickman et al., 1994, *Human Gene Therapy,* 5: 1477–1483; and Meyer et al., 1995, *Gene Therapy* 2: 450–460, the entireties of which are incorporated by reference herein).

Proteins or polypeptides which can be expressed by nucleic acid molecules delivered according to the present invention include enzymes, immunoglobulins, antibodies, toxins, antagonists, anti-angiogenesis proteins (e.g., Factor VIII or Factor IX) and the like. The compounds which can be provided are only limited by the availability of the nucleic acid sequence encoding a given protein or polypeptide. One skilled in the art will readily recognise that as more proteins and polypeptides become identified, their corresponding genes can be cloned into the gene expression vector(s) of choice, administered to a tissue of a recipient patient or other vertebrate, and expressed in that tissue to facilitate cell death.

In one aspect, a protein or fragment thereof having biological activity is administered directly to a target to facilitate cell death. In one embodiment, the protein is selected from the group consisting of an enzyme (e.g., such as a metabolic enzyme); a cytokine; a polyclonal or monoclonal antibody or an effective part thereof (e.g., a part which retains antigen binding specificity); a peptide hormone; a receptor; and a signalling molecule.

In embodiments where the cell-death facilitating protein is an antibody, the antibody can be an intact immunoglobulin as well as a antibody fragment such as Fv, a single chain Fv (scFv), a Fab or a F(ab')$_2$. The antibody can be natural, synthetic, or humanised. Preferably, antibodies are those which bind to and block the activity of a molecule required for cell viability. More preferably, a cell-death facilitating antibody is capable of binding to antigens in an intracellular environment, e.g., the antibody is an "intrabody" or "intracellular antibody." An "intracellular antibody" or an "intrabody" is an antibody which is capable of binding to its target or cognate antigen within the environment of a cell, or in an environment which mimics an environment within the cell.

Selection methods for directly identifying such "intrabodies" include the use of an in vivo two-hybrid system for selecting antibodies with the ability to bind to antigens inside mammalian cells. Such methods are described in International Patent Application number PCT/GB00/00876, incorporated herein by reference. Techniques for producing intracellular antibodies, such as anti-β-galactosidase scFvs, have also been described in Martineau et al., 1998, *J. Mol. Biol.* 280: 117–127 and Visintin et al., 1999, *Proc. Natl. Acad. Sci. USA* 96:11723–11728, the entireties of which are incorporated herein.

In one aspect, an antibody which inhibits the effects of VEGF can be used as a cell-death facilitating agent; for example, to prevent the vascularization of tumors, a process associated with the progression of cancer.

In another aspect, the cell-death facilitating agent is radioactive, i.e., the agent is a radionuclide which is used in radiotherapy. The radionuclide can be a radioisotope, including, but not limited to, cobalt-60, iodine-131, or a molecule such as a nucleic acid, polypeptide, or other molecule conjugated with such a radioisotope. As noted above, external radiation sources capable of delivering radionuclides to external or internal targets can be used to facilitate cell death in the treated target.

In some aspects, radioactive agents can be provided in the form of seeds, which can optionally include additional therapeutic agents (e.g., drugs, antibiotics, desired gene products, nucleic acids encoding desired gene products, and the like). In one aspect, a radioactive seed is delivered to a target through a medical access device (e.g., a catheter or endoscope or other medical access device) in combination with, or separate from, the delivery of ultrasound, or substantially prior to electrosensitisation. Radioactive seeds are known in the art and described in U.S. Pat. No. 6,203,524; U.S. Pat. No. 6,200,257; U.S. Pat. No. 6,159,143; and U.S. Pat. No. 6,132,359, the entireties of which are incorporated by reference herein.

It will be appreciated that it is not necessary for a single agent to be used, and that it is possible to utilize two or more cell-death facilitating agents, sequentially or simultaneously, to achieve cell death. Accordingly, the term "agent" also includes mixtures, fusions, combinations and conjugates, of atoms, molecules, and the like, as disclosed herein. For example, agents include, but are not limited to, a nucleic acid combined with a polypeptide; two or more polypeptides conjugated or fused to each other or mixed with each other; a protein conjugated to a biologically active molecule (which may be a small molecule such as a prodrug); or a combination of a biologically active molecule with an imaging agent.

Particularly useful classes of biological effector molecules include, but are not limited to, antibiotics, anti-inflammatory drugs, angiogenic or vasoactive agents, growth factors and cytotoxic agents (e.g., tumor suppressers). Cytotoxic agents of use in the invention include, but are not limited to, diptheria toxin, Pseudomonas exotoxin, cholera toxin, pertussis toxin, and the prodrugs peptidyl-p-phenylenediamine-mustard, benzoic acid mustard glutamates, ganciclovir, 6-methoxypurine arabinonucleoside (araM), 5-fluorocytosine, glucose, hypoxanthine, methotrexate-alanine, N-[4-(a-D-galactopyranosyl)
benyloxycarbonyl]-daunorubicin, amygdalin, azobenzene
mustards, glutamyl p-phenylenediamine mustard,
phenolmustard-glucuronide, epirubicin-glucuronide, vinca-cephalosporin, phenylenediamine mustard-cephalosporin,
nitrogen-mustard-cephalosporin, phenolmustard phosphate,
doxorubicin phosphate, mitomycin phosphate, etoposide
phosphate, palytoxin-4-hydroxyphenyl-acetamide,
doxorubicin-phenoxyacetamide, melphalan-phenoxyacetamide, cyclophosphamide, ifosfamide or analogues thereof. If a prodrug is applied to the target cell, tissue or tissue mass in inactive form, a second biological effector molecule may be applied. Such a second biological effector molecule is usefully an activating polypeptide which converts the inactive prodrug to active drug form, and which activating polypeptide is selected from the group that includes, but is not limited to, viral thymidine kinase (encoded by Genbank Accession No. J02224), carboxypeptidase A (encoded by Genbank Accession No. M27717), α-galactosidase (encoded by Genbank Accession No. M13571), β-glucuronidase (encoded by Genbank Accession No. M15182), alkaline phosphatase (encoded by Genbank Accession No. J03252 J03512), or cytochrome P-450 (encoded by Genbank Accession No. D00003 N00003), plasmin, carboxypeptidase G2, cytosine deaminase, glucose oxidase, xanthine oxidase, β-glucosidase, azoreductase, t-gutamyl transferase, β-lactamase, or penicillin amidase. Either the polypeptide or the gene encoding it may be administered; if the latter, both the prodrug and the activating polypeptide may be encoded by genes on the same recombinant nucleic acid construct.

Preferably the biological effector molecule is selected from the group consisting of a protein, a polypeptide, a peptide, a nucleic acid, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid and a carbohydrate or a combination thereof (e.g., chromosomal material comprising both protein and DNA components or a pair or set of effectors, wherein one or more convert another to active form, for example catalytically).

The biological effector molecule is preferably an immunomodulatory agent or other biological response modifier. Also included are polynucleotides which encode metabolic enzymes and proteins, including antiangiogenesis compounds, e.g., Factor VIII or Factor IX.

Cytotoxics

A highly preferred embodiment of the invention encompasses the use of one or more agents which facilitate cell death, whether alone or in combination with each other, together with ultrasound/electric field treatment as described. Preferred agents include cytotoxics and cytokines.

"Cytotoxicity" refers to the cell killing property of a chemical compound (such as a food, cosmetic, or pharmaceutical) or a mediator cell (cytotoxic T cell). In contrast to necrosis and apoptosis, the term cytotoxicity need not necessarily indicate a specific cellular death mechanism. For example, cell mediated cytotoxicity (that is, cell death mediated by either cytotoxic T lymphocytes [CTL] or natural killer [NK] cells) combines some aspects of both necrosis and apoptosis. The terms "cytotoxic" and "cytoxic drug" are used interchangeably, and refer to any of a group of drugs that are toxic to cells and cause cell death or prevent any cell process such as cell growth, proliferation, or replication. The latter are also referred to as "cytostats" or "cytostatic drugs".

Preferably, the cytotoxic comprises chemotherapeutic agents having an antitumor effect. Cytotoxics are used mainly to treat cancer, although some have other uses (such as for treatment of other disorders, such as psoriasis and rheumatoid arthritis). Cancer treatment with cytotoxics is known as chemotherapy and has a variety of purposes. The cytotoxics may be used to shrink a tumor before surgery (neoadjuvant chemotherapy); they may be used after the primary tumor has been treated with surgery or radiotherapy to prevent the spread and growth of secondary tumors (adjuvant chemotherapy), or they may be the main treatment for the disease. Chemotherapy may be given to cure the disease or, if cure is not possible, to control its symptoms (palliative chemotherapy).

Cytotoxics suitable for use for the preferred embodiments of the present invention include alkylating drugs, antimetabolites, vinca alkaloids, cytotoxic antibiotics, platinum compounds (e.g. carboplatin), taxanes, topoisomerase inhibitors, procarbazine, crisantaspase, hydroxyurea, Rituximab (a monoclonal antibody) and aldesleukin (an interleukin). Other preferred examples of cytotoxics include bleomycin, neocarcinostatin, suramin, doxorubicin, carboplatin, taxol, mitomycin C, cisplatin, Azathioprine, (Imuran), Cyclophosphamide, (Cytoxan), Methotrexate (Rheumatrex), as well as other cytotoxic drugs related to cyclophosphamide (Cytoxan) including chlorambucil (Leukeran) and nitrogen mustard (Mustargen).

Sex hormones have been used to treat cancer, and may also be used in the invention. Tumors of the prostate gland are often stimulated by male sex hormones (the androgens) and so these cancers may be treated with oestrogens (to oppose the androgens) or with anti-androgens. Analogues of gonadorelin, such as buserelin, goserelin, leuprorelin, and triptorelin, may also be used. Some breast cancers are stimulated by oestrogens; such cancers respond to the oestrogen antagonists tamoxifen and toremifene or to aromatase inhibitors. Any of the above cytotoxics may be employed in the preferred methods of the present invention.

Also included within the term "cytotoxic" are cells such as Cytotoxic T lymphocytes (CTL) and Natural Killer (NK) cells. Furthermore, it has been found that compounds which inhibit the effects of VEGF, such as PTK787/ZK 222584, have the potential to provide effective and well-tolerated therapies for the treatment of solid tumors (Wood, 2000, *Medicina* (*B Aires*) 60(*Suppl*) 2: 41–7). Accordingly, the use of such compounds as cell-death facilitating agents is also envisaged.

The cytotoxic may be taken orally or given by injection or infusion. In general, cytotoxics may be administered in any suitable manner. Preferred routes of administration include administration systemically, orally and nasally. A highly preferred route is local administration to the target tissue (e.g., through a catheter or other medical access device, through an open surgical field, and the like). Any suitable formulation, as disclosed in further detail below, may be employed. A combination of two, three, or more cytotoxics, optionally together with one, two, three or more cytokines (as disclosed in further detail elsewhere) may be given. The effects of cytotoxics may need to be carefully monitored and blood tests carried out regularly.

Cytokines

In a further embodiment, the cell-death-facilitating agent comprises an agent which is capable of modulating an immune response of the patient. This modulation can take the form of stimulating the proliferation and/or activity of one or more immune cells, e.g., boosting or reinforcing an immune response, or can be via recruitment of immune cells to a target site. Preferably, such an immune response is directed against one or more cells at the target site, preferably, cells which have been exposed to sensitisation and/or disruption. More preferably, the cell is an electrosensitised cell which has been exposed to ultrasound, most preferably, a disrupted or ablated cell which has been so exposed. In a highly preferred embodiment of the invention, administration of a cell-death facilitating agent results in a cell being destroyed by means of one or more components of the patient's immune system.

In one aspect, agents preferably stimulate host immune responses through recruitment of killer cells such as cytotoxic T-cells and dendritic cells to a target site. For example, immunogens or antigens may be administered to the patient as part of the therapy described herein, to enhance cell killing.

In one aspect, the antigen is a cancer-specific antigen or tumor antigen. Tumor antigens are a class of protein markers that tend to be expressed to a greater extent by transformed tumor cells than by non-transformed cells. As such, tumor antigens may be expressed by non-tumor cells, although usually at lower concentrations or during an earlier developmental stage of a tissue or organism. Tumor antigens include, but are not limited to, prostate specific antigen (PSA; Osterling, 1991, *J. Urol.* 145: 907–923), epithelial membrane antigen (multiple epithelial carcinomas; Pinkus et al., 1986, *Am. J. Clin. Pathol.* 85: 269–277), CYFRA 21-1 (lung cancer; Lai et al., 1999, *Jpn. J. Clin. Oncol.* 29: 421–421) and Ep-CAM (pan-carcinoma; Chaubal et al., 1999, *AntiCancer Res.* 19: 2237–2242). Additional examples of tumor antigens include CA125 (ovarian cancer), intact monoclonal immunoglobulin or light chain fragments (myeloma), and the beta subunit of human chorionic gonadotropin (HCG, germ cell tumors).

A sub-category of tumor antigens includes the oncofetal tumor antigens. The oncofetal tumor antigens alphafetoprotein and carcinoembryonic antigen (CEA) are usually only highly expressed in developing embryos, but are frequently highly expressed by tumors of the liver and colon, respectively, in adults. Other oncofetal tumor antigens include, but are not limited to, placental alkaline phosphatase (Deonarain et al., 1997, *Protein Eng.* 10: 89–98; Travers and Bodmer, 1984, *Int. J. Cancer* 33: 633–641), sialyl-Lewis X (adenocarcinoma, Wittig et al., 1996, *Int. J. Cancer* 67: 80–85), CA-125 and CA-19 (gastrointestinal, hepatic, and gynecological tumors; Pitkanen et al., 1994, *Pediatr. Res.* 35: 205–208), TAG-72 (colorectal tumors; Gaudagni et al., 1996, *Anticancer Res.* 16: 2141–2148), epithelial glycoprotein 2 (pan-carcinoma expression; Roovers et al., 1998, *Br. J. Cancer.* 78: 1407–1416), pancreatic oncofetal antigen (Kithier et al., 1992, *Tumor Biol.* 13: 343–351), 5T4 (gastric carcinoma; Starzynska et al., 1998, *Eur. J. Gastroenterol. Hepatol.* 10: 479–484; alphafetoprotein receptor (multiple tumor types, particularly mammary tumors; Moro et al., 1993, *Tumour Biol.* 14: 11–130), and M2A (germ cell neoplasia; Marks et al., 1999, *Brit. J. Cancer* 80: 569–578).

The term "cytokine" may be used to refer to any of a number of soluble molecules (e.g., glycoproteins) released by cells of the immune system, which act nonenzymatically through specific receptors to regulate immune responses. Cytokines resemble hormones in that they act at low concentrations bound with high affinity to a specific receptor. Preferably, the term "cytokine" refers to a diverse group of soluble proteins and peptides which act as humoral regulators at nano- to picomolar concentrations and which, either under normal or pathological conditions, modulate the functional activities of individual cells and tissues.

Particular examples of cytokines which are suitable for use in the present invention include one or more of: interleukin, lymphokine, interferon, Colony Stimulating Factors (CSFs) such as Granulocyte-Colony Stimulating Factor (G-CSF), Macrophage-Colony stimulating factor (M-CSF), Granulocyte-Macrophage-Colony stimulating factor (GM-CSF), GSF, Platelet-Activating Factors (PAF), and Tumor Necrosis Factor (TNF).

Thus, interleukins such as IL-1, IL-2 and IL-4, as well as interferons such as IFN-α, IFN-β and IFN-γ may be used in the methods described here. Tumor necrosis factors TNF-α (cachetin), TNF-β (lymphotoxin) also may be suitably employed.

Preferred cytokines are those which are capable of recruiting immune responses, for example, stimulation of dendritic cell or cytotoxic T cell activity, or which are capable of recruiting macrophages to the target site. In a highly preferred embodiment of the invention, the cytokine comprises IL-2, GM-CSF or GSF.

Apoptosis

Cell death can occur by either of two distinct mechanisms, necrosis or apoptosis. In addition, certain chemical compounds and cells are said to be cytotoxic to the cell, that is, to cause its death. According to a preferred aspect of the invention, exposure of cells to a sensitising stimulus and a disrupting stimulus, such as an electric field and ultrasound results in at least a proportion of the cells undergoing cell death by apoptosis. Preferably, at least 20% of cell death as a result of treatment by the methods according to the invention is apoptotic. More preferably, at least 40%, 60%, 80% or more, most preferably greater than 95% of cell which die are apoptotic when treated with electric field and ultrasound.

"Necrosis" (also referred to as "accidental" cell death) refers to the pathological process which occurs when cells are exposed to a serious physical or chemical insult. Necrosis occurs when cells are exposed to extreme variance from physiological conditions (e.g., hypothermia, hypoxia) which may result in damage to the plasma membrane. Under physiological conditions direct damage to the plasma membrane is evoked by agents like complement and lytic viruses. Necrosis begins with an impairment of the cell's ability to maintain homeostasis, leading to an influx of water and extracellular ions. Intracellular organelles, most notably the mitochondria, and the entire cell swell and rupture (cell lysis). Due to the ultimate breakdown of the plasma membrane, the cytoplasmic contents including lysosomal enzymes are released into the extracellular fluid. Therefore, in vivo, necrotic cell death is often associated with extensive tissue damage resulting in an intense inflammatory response.

"Apoptosis" ("normal" or "programmed" cell death) refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine dependent tissue atrophy. Cells undergoing apoptosis show characteristic morphological and biochemical features. These features include chromatin aggregation, nuclear and cytoplasmic condensation, partition of cytoplasm and nucleus into membrane bound vesicles (apoptotic bodies) which contain ribosomes, morphologically intact mitochondria and nuclear material. In vivo, these apoptotic bodies are rapidly recognized and phagocytized by either macrophages or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis".

Table 1 summarises the various observable differences between necrosis and apoptosis. Any of these differences, alone or in combination may be assayed in order to determine whether cell death is occurring by apoptosis or by necrosis.

Duke & Cohen, 1986, *Lymphokine Res.* 5: 289; Trauth et al., 1994, *Eur. J. Cell. Biol.* 63: 32, Suppl 40; Matzinger, 1991, *J. Immunol. Methods* 145: 185; Kaeck, 1993, *Anal. Biochem.* 208: 393; Prigent et al., 1993, *J. Immunol. Methods* 160: 139; Huang & Plunkett, 1992, *Anal. Biochem.* 207: 163; Bortner et al., 1995, *Trends Cell Biol.* 5: 21; Gold et al., 1994, *Lab. Invest.* 71: 219.

Apoptosis and cell-mediated cytotoxicity are characterised by cleavage of the genomic DNA into discrete fragments prior to membrane disintegration. Accordingly, apoptosis may be assayed by measuring DNA fragmentation, for example, by observing the presence of DNA ladders characteristic of apoptotic cells. DNA fragments may be identified by gel electrophoresis of nucleic acids from samples derived from populations of cells on an agarose or

TABLE 1

Differential Features Of Necrosis And Apoptosis

| Features/Significance | Necrosis | Apoptosis |
|---|---|---|
| Morphological | Loss of membrane integrity which begins with swelling of cytoplasm and mitochondria and ends with total cell lysis; No vesicle formation but complete lysis and disintegration (swelling) of organelles. | Membrane blebbing, but no loss of integrity; Chromosome aggregation is observed at the nuclear membrane; In the initial stages, the cytoplasm shrinks and the nucleus condenses; Late in the process, the cell fragments into smaller bodies and membrane bound vesicles (apoptotic bodies) form; and Mitochondria become leaky due to pore formation which is mediated by proteins of the bcl-2 family. |
| Biochemical | Loss of regulation of ion homeostasis; No energy requirement (passive process, also occurs at 4° C.); Random digestion of DNA (smear of DNA after agarose gel electrophoresis); and Postlytic DNA fragmentation (= late event of death). | Tightly regulated process involving activation and enzymatic steps; Energy (ATP)-dependent (active process, does not occur at 4° C.); Non-random mono- and oligonucleosomal length fragmentation of DNA (Ladder pattern after agarose gel electrophoresis); Prelytic DNA fragmentation Release of various factors (cytochrome C, AIF) into cytoplasm by mitochondria; Activation of caspase cascade; and Alterations in membrane asymmetry (i.e., translocation of phosphatidyl-serine from the cytoplasmic to the extracellular side of the membrane). |
| Physiological significance | Affects groups of contiguous cells; Evoked by non-physiological disturbances (complement attack, lytic viruses, hypothermia, hypoxia, ischemica, metabolic poisons); Phagocytosis by macrophages; and Accompanied by significant inflammatory response. | Affects individual cells; Induced by physiological stimuli (lack of growth factors, changes in hormonal environment); Phagocytosis by adjacent cells or macrophages; and No inflammatory response. |

Reference is made to the following documents, which describe apoptosis in detail, as well as various assays for measuring cell death by apoptosis: Schwartzman and Cidlowski, 1993, *Endocrine Rev.* 14:133; Vermes and Haanan, 1994, *Adv. Clin. Chem.* 31: 177; Berke, 1991, *Immunol. Today* 12: 396; Krähenbühl and Tschopp, 1991, *Immunol. Today* 12: 399; Van Furth and Van Zwet, 1988, *J. Immunol. Methods* 108: 45. Cohen, 1993, Apoptosis. *Immunol. Today* 14: 126; Savill et al., 1989, *J. Clin. Invest.* 83: 865; Wyllie, 1980, *Nature* 284: 555; Leist et al., 1994, *Biochemica* 3: 18-20; Fraser and Evan, 1996, *Cell* 85: 781–784; Duke, 1983, *Proc. Natl. Acad. Sci. USA* 80: 6361;

acrylamide gel and staining of the gel with ethidium bromide. DNA fragments spaced 180 bp apart represent the "rungs" of the ladder on the gel.

DNA fragments can be quantified by detecting histone-complexed DNA fragments. In one aspect, an ELISA-based assay is used. For example, cells can be pelleted from a sample by centrifugation and the supernatant which contains DNA which has leaked through the membranes of necrotic cells, discarded. Cells can then be resuspended and incubated in lysis buffer to obtain a nucleosome fraction by centrifugation. An aliquot of a nucleosome fraction can then be transferred to a streptavidin-coated well of a microtiter plate and nucleosomes can be bound with two monoclonal antibodies, biotin labeled anti-histone and peroxidase labeled anti-DNA antibodies. Antibody-nucleosome complexes are bound to the microtiter plate by the streptavidin via the histone part of the complex and the plate is washed to remove cell components that are not immunoreactive (e.g., 3 times). The microtiter plate is then incubated with a peroxidase substrate (e.g., such as ABTS®) and the DNA portion of the nucleosome complex bound to peroxidase will react with the substrate to form colored product. Colored product can be quantitated using appropriate standards spectrophotometrically and can provide a measure of the amount of fragmented DNA and hence of apoptotic cells in the sample. It should be obvious to those of skill in the art that any number of binding polypeptides and their binding partners can be used in place of streptavidin: biotin and that reporting enzymes or detectable molecules other than peroxidase can be used, and are encompassed within the scope of the invention.

Several proteases are involved in the early stages of apoptosis, therefore, apoptosis also may be assayed for by detecting the presence of and/or activity of apoptosis-induced proteases such as caspases (e.g., caspase 3). For example, cellular lysates can be evaluated by an in vitro enzyme assay in which caspase is captured (e.g., on a solid phase comprising a binding partner which specifically binds to caspase) and the proteolytic cleavage of a suitable substrate can be measured. In vitro assays are described in Segal et al., 2001, *Am. J. Physiol. Cell. Physiol.* 281(4): C1196–C1204. In one aspect, the substrate is a linker polypeptide (about 6 to 18 amino acids) with a protease cleavage site. The polypeptide is flanked at one end with an energy donor (e.g., a chemiluminescent energy donor such as aequorin) and at the other end with an energy acceptor (e.g., such as green fluorescent protein (GFP) or enhanced GFP). The presence of the protease in a sample will trigger a shift in the emission spectra of the chimeric polypeptide as it is cleaved which can be detected and quantitated and correlated to the presence and amount of the protease using appropriate standards (see, e.g., Waud et al., 2001, *Biochem J.* 357(Pt 3): 687–697).

Cleavage of an in vivo caspase substrate such as PARP (Poly-ADP-Ribose-Polymerase) also can be measured. For example, cleaved fragments of PARP may be detected with a suitable antibody such as an anti PARP antibody (see, e.g., de Boer et al., 2000, *J. Card. Fail.* 6(4): 330–337).

Other protease assays and DNA fragmentation assays also are suitable for assaying apoptosis in cell populations. Such assays are known and routine in the art.

Methods for studying apoptosis in individual cells are also available, such as ISNT and TUNEL enzymatic labeling assays which are known in the art. As noted above, extensive DNA degradation is a characteristic event which often occurs during the early stages of apoptosis. Cleavage of DNA yields double-stranded, low molecular weight DNA fragments (mono- and oligonucleosomes) as well as single strand breaks ("nicks") in high molecular weight-DNA. In TUNEL, such DNA strand breaks are detected by enzymatic labeling of the free 3'-OH termini with suitable modified nucleotides (such as X-dUTP, X=biotin, DIG or fluorescein). Suitable labeling enzymes include DNA polymerases (nick translation polymerases) in ISNT, e.g., where "in situ nick translation" is performed, and terminal deoxynucleotidyl transferase in TUNEL, e.g., where end labeling is performed (see, e.g., Huang, P. & Plunkett, W., 1992, Anal. Biochem. 207: 163; Bortner et al., 1995, Trends Cell Biol. 5: 21).

Apoptosis also may be assayed by measuring membrane alterations, including: loss of terminal sialic acid residues from the side chains of cell surface glycoproteins, exposure of new sugar residues; emergence of surface glycoproteins that may serve as receptors for macrophage-secreted adhesive molecules such as thrombospondin; and loss of asymmetry in cell membrane phospholipids, altering both the hydrophobicity and charge of the membrane surface.

In particular, the human anticoagulant annexin V is a 35–36 kilodalton, Ca2+-dependent phospholipid-binding protein that has a high affinity for phosphatidylserine (PS). In normal viable cells, PS is located on the cytoplasmic surface of the cell membrane. However, in apoptotic cells, PS is translocated from the inner to the outer leaflet of the plasma membrane, thus exposing PS to the external cellular environment. Annexin V may therefore be used to detect phosphatidylserine asymmetrically exposed on the surface of apoptotic cells (Homburg et al., 1995, *Blood* 85: 532; Verhoven et al., 1995, *J. Exp. Med.* 182: 1597).

DNA stains such as DAPI, ethidium bromide and propidium iodide, and the like, also may be used for differential staining to distinguish viable and non-viable cells. Profiles of DNA content additionally may be used since permeabilized apoptotic cells leak low molecular weight DNA. In one aspect, detection of "sub-G 1 peaks", or "A 0" cells (cells with lower DNA staining than that of G 1 cells) by flow cytometry is used to identify apoptotic cells in a sample. Morphological changes characteristic of apoptosis also may be detected in this manner.

Detection of apoptosis-related proteins such as ced-3, ced-4, ced-9 (Ellis and Horvitz, 1986, *Cell* 44: 817–829; Yuan and Horvitz, 1990, *Dev. Biol.* 138: 33–41; Hentgartner et al., 1992, *Nature* 356: 494–499.); Fas (CD95/Apo-1; Enari et al., 1996, *Nature* 380: 723–726), Bcl–2 (Baffy et al., 1993, *J. Biol. Chem.* 268: 6511–6519; Miyashita and Reed, 1993, *Blood* 81: 151–157; Oltvai et al., 1993, *Cell* 74: 609–619); p53 (Yonish-Rouach, et al., 1991, *Nature* 352: 345–347), e.g., such as by the use of antibodies, also may be used to assay apoptosis.

Pharmaceutical Compositions

While it is possible for the cell-death facilitating agent or agents to be administered alone, it is preferable to formulate the active ingredient as a pharmaceutical composition. The composition may include the cell-death facilitating agent, a structurally related compound, or an acidic salt thereof. The pharmaceutical compositions of the invention comprise an effective amount of cell-death facilitating agent, together with one or more pharmaceutically-acceptable carriers. The effective amount will vary depending upon the particular conditions of treatment and cell type, as well as other factors, including the age and weight of the patient, the general health of the patient, the severity of the symptoms, and whether the cell-death facilitating agent is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporisable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

Pharmaceutical compositions include those suitable for topical and oral administration, with topical formulations being preferred where the tissue affected is primarily the skin or epidermis (for example, a skin tumor or melanoma). Topical formulations include those pharmaceutical forms in which the composition is applied externally by direct contact with the skin surface to be treated. A conventional pharmaceutical form for topical application includes a soak, an ointment or water-in-oil emulsion, a cream, a lotion, a paste, a gel, a stick, a spray, an aerosol, a bath oil, a solution and the like. Topical therapy is delivered by various vehicles. The choice of vehicle can be important and generally is related to whether an acute or chronic disease is to be treated. Other formulations for topical application include shampoos, soaps, shake lotions, and the like, particularly those formulated to leave a residue on the underlying skin, such as the scalp (see, Arndt et al, 1993, *Dermatology In General Medicine* 2: 2838).

In general, the concentration of the cell-death facilitating agent in a topical formulation is in an amount of about 0.5 to 50% by weight of the composition, preferably about 1 to 30%, more preferably, about 2–20%, and most preferably, about 5–10%. The concentration used can be in the upper portion of the range initially, as treatment continues, the concentration can be lowered or the application of the formulation may be less frequent. Topical applications are often applied twice daily. However, once-daily application of a larger dose or more frequent applications of a smaller dose may be effective.

The stratum corneum may act as a reservoir and allow gradual penetration of a drug into the viable skin layers over a prolonged period of time where the composition is administered topically. A skin penetration enhancer which is dermatologically acceptable and compatible with the cell-death facilitating agent can be incorporated into the formulation to increase the penetration of the active compound(s) from the skin surface into epidermal keratinocytes. Skin penetration enhancers are well known in the art. For example, dimethyl sulfoxide (U.S. Pat. No. 3,711,602); oleic acid, 1,2-butanediol surfactant (Cooper, 1984, *J. Pharm. Sci.*, 73:1153–1156); a combination of ethanol and oleic acid or oleyl alcohol (EP 267,617); 2-ethyl-1,3-hexanediol (WO 87/03490); decyl methyl sulphoxide and Azone® (Hadgraft, 1996, *Eur. J. Drug. Metab. Pharmacokinet.* 21: 165–173); alcohols, sulphoxides, fatty acids, esters, pyrrolidones, urea and polyols (Kalbitz et al, 1996, *Pharmazie* 51: 619–637). Terpenes such as 1,8-cineole, menthone, limonene and nerolidol (Yamane, 1995, *J. Pharmacy & Pharmocology* 47: 978–989); Azone® and Transcutol (Harrison et al, 1996, *Pharmaceutical Res.* 13: 542–546); and oleic acid, polyethylene glycol and propylene glycol (Singh et al, 1996, *Pharmazie* 51: 741–744) are known to improve skin penetration of an active ingredient.

For some applications, it is preferable to administer a long acting form of cell-death facilitating agent using formulations known in the art, such as polymers. The cell-death facilitating agent can be incorporated into a dermal patch (Junginger, 1992, *Acta Pharmaceutica Nordica* 4: 117 Thacharodi et al, 1995, *Biomaterials* 16: 145–148; Niedner, 1988, *Hautarzt* 39: 761–766) or a bandage, according to methods known in the art, to increase the efficiency of delivery of the drug to the areas to be treated. Optionally, topical compositions can have additional excipients, for example, preservatives such as methylparaben, benzyl alcohol, sorbic acid or quaternary ammonium compound; stabilizers such as EDTA; antioxidants such as butylated hydroxytoluene or butylated hydroxanisole; and buffers such as citrate and phosphate.

The pharmaceutical compositions also can be administered in an oral formulation in the form of tablets, capsules or solutions. In general, the daily oral dose of cell-death facilitating agent is less than 1200 mg, and more than 100 mg. The preferred daily oral dose is about 300–600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the compositions are prepared by uniformly and intimately bringing into association the cell-death facilitating agent with liquid carriers or finely divided solid carriers or both, and, as necessary, shaping the product. The active ingredient can be incorporated into a variety of basic materials in the form of a liquid, powder, tablets or capsules, to give an effective amount of active ingredient.

Other therapeutic agents suitable for use herein are any compatible drugs that are complementary with the administration of cell-death facilitating agents. As an example, treatment of a skin cell proliferation disease (e.g., melanoma, psoriasis, etc.) by administering a cell-death facilitating agent to a target site comprising sensitised, disrupted cells can be combined with the topical administration of corticosteroids, calcipotrine, or coal tar preparations. Systemic treatments using methotrexate, retinoids, cyclosporin A and photochemotherapy also can be provided. Combined treatments may be especially important for treatment of an acute or a severe disease. Formulations or compositions utilised in a combination therapy may be administered simultaneously or sequentially with one or more of: cell sensitisation, disruption, and administration of cell-death facilitating agents.

Assays

The observation that cells exposed to electric fields and ultrasound exhibit cell death through apoptosis may be used as the basis of assays to identify useful molecules and targets for therapy.

One such assay is used to identify molecules which are capable of modulating (e.g., enhancing or inhibiting) the expression or function of biomolecules (e.g., genes, gene products, and other cellular constituents) involved in apoptosis of a cell. As used herein, a biomolecule "involved in apoptosis" is a biomolecule whose proper expression, localisation, and/or function is required to trigger any of the physiological responses which occur during apoptosis. For example, assays which identify molecules which modulate (i.e., induce, enhance, or inhibit) the expression of and/or the protease activity of caspases or other apoptosis proteases are encompassed within the instant invention.

The assays, in general, involve contacting a cell with a candidate molecule, i.e., a molecule or compound which is suspected of having apoptosis-modulating activity. Such candidate molecules may be provided in the form of libraries such as combinatorial libraries (e.g., phage display libraries) as are known in the art. The cell is then treated by exposure to a sensitising stimulus and a disrupting stimulus (e.g., such as an electric field and ultrasound) as described above, at levels which are known, or which have been determined to be, capable of inducing apoptosis in cells of the particular type or characteristics being used in the assay. The progress (early, middle or late stage) or degree of apoptosis (e.g., amount of apoptotic bodies, and the like) is observed to identify molecules which are capable of inducing, enhancing, inhibiting, or stopping, apoptosis of the cells. Molecules identified by such an assay are useful as drugs to enhance or inhibit apoptotic cell death, and may be used in therapies of diseases in which apoptotic cell death is part of the pathology. In a preferred embodiment, the degree of inhibition or enhancement is any which is determined to be statistically significant when compared to the degree of apoptosis in a control sample by the particular assay used, using 95% confidence levels to establish differences as significant. More preferably, the degree of enhancement or inhibition of apoptosis results in a level of apoptosis which is at least 10%, at least 20%, at least 30%, at least 40%, at least 50%, at least 60%, at least 70%, at least 80%, at least 90%, or at least 100%, higher or lower, respectively, than the amount of apoptosis observed in a control sample. Preferably, the degree of enhancement or inhibition is at least 1.5-fold, at least 2-fold, at least 10-fold, at least 20-fold, at least 30-fold, at least 40-fold, at least 50-fold, higher or lower, respectively, than the level of apoptosis in a control sample.

In another aspect, the invention provides an assay which is capable of identifying genes involved in regulating apoptosis, or genes which are themselves involved in apoptotic processes. Such an assay essentially relies on modulating the function of a gene or gene product which is suspected of being involved in, or in regulating, an apoptotic process. By "gene product" is meant an RNA transcribed from the gene, or a polypeptide product of the gene, or a processed, cleaved or modified form thereof.

In one aspect, gene function is disrupted. For example, the gene can be knocked out by mutation, or by introducing an inhibitor of a product of the gene into a cell. For example, an antisense RNA, a ribozyme, or a chemical inhibitor can be introduced into the cell using methods routine in the art. The cell is then exposed to a sensitising stimulus and disrupting stimulus at levels which are known, or have been determined to be, capable of inducing apoptosis in cells of the same particular type and characteristics (such levels can be readily optimised in control assays using parameters described above as starting points). The presence, degree, and/or rate of apoptosis can be observed. In one aspect, cells are mutagenized randomly (using chemical agents or by transformation with nucleic acids) and cells are selected for which show enhanced or decreased levels of apoptosis relative to control cells (cells which have been sensitised and disrupted but not otherwise mutagenized or which have not had inhibitory agents introduced).

Similarly, gene function may be enhanced and the effect of the enhancement on apoptosis assayed. For example, a gene may be overexpressed (e.g., by introducing multiple copies of the gene into a cell), turned on ectopically (e.g., expressed in a cell in which it is not normally expressed by operably linking to a heterologous promoter which is active in the cell), or mutagenized to enhance the accumulation of its gene product (e.g., by enhancing the stability of its encoded RNA or polypeptide) by using methods routine in the art. The cells are then exposed to disrupting and sensitising stimuli and the presence, degree and/or rate of apoptosis observed.

Candidate genes which are suspected of being involved in apoptosis may then be used as targets for drug discovery programs, to identify candidate modulators of apoptosis by screening for compounds which affect the expression of the gene and/or the activity of the gene's product(s). Such assays are routine in the art. Lead compounds identified which enhance or inhibit the activity of the gene product(s) can then be tested in vitro or in vivo using model animal system to determine the effects of the compounds on pathologies that involved the misregulation of apoptotic processes.

System

The invention further relates to a system suitable for disrupting a cell, for example, within an organism. Such a system comprises an electrosensitisation module and an ultrasound generating module, which can be provided separably or as integral or removable units in fluid communication with each other (e.g., the system can be a flow-through device). The electrosensitisation module of the system is capable of sensitising a nucleated cell to render it susceptible to disruption by an energy source. Preferably, the electrosensitisation module is capable of generating electric field energy to electrosensitise a nucleated cell such that it is rendered more susceptible to disruption by ultrasound than an unsensitised cell.

The electrosensitisation module preferably comprises an electric field generator. In one aspect, the generator provides an electric field which can electrosensitise a cell but which cannot electroporate a cell. The generator may be set to provide electrical field strengths and pulses for electrosensitisation by means of a processor in communication with the electric field generator. In a particularly preferred embodiment, the electric field generator when activated delivers direct current at low voltage to the electrosensitisation module. Preferably, the electric field strength delivered is about 1 V/cm, preferably 5 V/cm to 100 V/cm more, and can be up to 10 kV/cm under in vivo conditions. Preferably, electric field strength is between 10 V/cm and 20 V/cm, e.g., 10, 11, 12, 13, 14, 15, 16, 17, 18, 19 or 20 V/cm. Electric field strengths also may be measured in terms of current; preferably, the current applied is between 100 $\mu$A to 200 mA, preferably between 1 mA and 10 mA.

Preferably, the electric field generator generates electric field energy to the electrosensitisation module which is sufficient to electrosensitise a nucleated cell to ultrasound energy in an organism, such that electrosensitised cell is rendered susceptible to ultrasound disruption at a frequency and energy sufficient to cause disruption of the electrosensitised cell but insufficient to cause disruption of unsensitised cells. The electric field generator may deliver one or more pulses of electrical energy to the sensitisation module.

The electric field generator is preferably in communication with a processor which controls delivery of electric fields of suitable strength to the electrosensitisation module. The processor may be pre-programmed or may be programmed by a user to automatically prevent the delivery of electric fields to the electrosensitisation module at strengths higher than optimal for electrosensitisation. In one aspect, the electrosensitisation module is prevented from delivering electric fields at levels which would electroporate the cell.

The ultrasound generating module of the system is preferably capable of generating ultrasound energy to selectively disrupt a cell in an organism, in which the cell has previously been electrosensitised by exposure to electric field energy. The ultrasound generator more preferably generates ultrasound energy to selectively disrupt a cell in an organism, in which the cell has previously been electrosensitised by exposure to electric field energy. Preferably, ultrasound is delivered at a frequency and energy sufficient to cause disruption of the electrosensitised cell but insufficient to cause disruption of unsensitised cells.

The ultrasound generator is capable of generating ultrasound at a power level of from about 0.05 W/cm$^2$ to about 100 W/cm$^2$. In one aspect, the ultrasound generator delivers low intensity ultrasound at levels of 0.125–4 W/cm$^2$, or at levels from 100 mW/cm$^2$ to 750 mW/cm$^2$.

In one aspect, the electrosensitisation module comprises a housing which defines a lumen and the ultrasound module is positioned in the lumen such that both the electric field generator and ultrasound module can deliver the appropriate stimuli to the same target. Preferably, the electric field generator comprises one or more electrodes, which may be in the form of plates or an array of needles and/or which may themselves define the lumen in which the ultrasound module is positioned.

Figure 4:
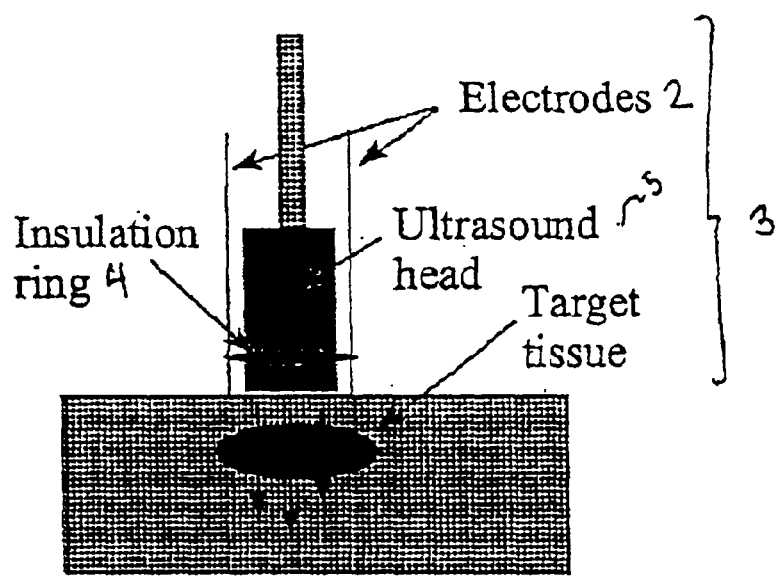
FIG. 4 is a diagram of an apparatus in accordance with the present invention.

A preferred embodiment of an apparatus 1 is shown in FIG. 4. Such an apparatus 1 comprises an electrode array 2 (which may be a double or multiple needle array with each diagonal representing opposing poles) set around and insulated from an ultrasound delivery device 3 comprising an ultrasound head 5. Preferably, the apparatus comprises an insulation ring 4 consisting of a material which absorbs ultrasound which insulates the electrodes 2 from short circuit discharge. The size of the apparatus may vary from a device suitable for treatment of surface lesions to a device which may be inserted into the body using a medical access device such as a catheter, endoscope, or laparoscope.

If used with a medical access device, the medical access device can comprise one or more of: an irrigation source, irrigation channels, an optical system comprising optical elements for directing light to a target and receiving light from a target and including one or more light focussing elements. The device can additionally include cutting elements, for example to render particular portions of a target more accessible to disruption. The medical access device can be in communication with a processor which can activate the electrosensitisation module and/or ultrasound module and/or control the amount of time and the strength/ frequency/power of energy delivered by the electrosensitisation module and/or ultrasound module.

Discharge of the electric pulse itself can be accomplished using a suitable electrical source or power pack and ultrasound can be delivered before, during, or after, delivery of electric pulses.

It should be obvious to those of skill in the art that the configuration of the apparatus can vary to suit particular types of targets. For example, the electric field generator can consist of an insulated microelectrode inserted into a target tissue (e.g., such as a tumor mass) and an opposing electrode array mounted onto an ultrasound head 4 inserted into the surrounding non-target tissues. In some applications, such as in vitro or ex vivo applications, the electrosensitisation module and the ultrasound module can be connected to each other by a reversibly sealable connecting element, and a cell can be transported from one module to another, such as by diffusion through a medium when the connecting element is not sealed, or by application of a force, such as pressure or gravity, on the medium in the electrosensitisation module, which forces the medium into the ultrasound module when the connecting element is not sealed.

The size of the device may vary from a device suitable for treatment of surface lesions to a device which may be inserted into the body using catheterisation or laparoscopy.

Discharge of the electric pulse is accomplished using a suitable electrical source or power pack and ultrasound will be delivered before, during or after delivery of electric pulses.

The electrode array may be configured differently to suit a particular therapeutic application. For example, it may consist of an insulated microelectrode which can be inserted into a target tissue and an opposing electrode array, mounted onto an ultrasonic head inserted into the surrounding tissues. Various electrode arrays are known in the art, and are described in, for example, U.S. Pat. No. 5,720,921; WO 99/62592; WO 98/56893; U.S. Pat. No. 6,041,252; and U.S. Pat. No. 5,873,849. The system as described herein may employ any one or more of such electrode configurations.

The electrosensitisation module also may comprise a delivery element comprising a housing defining a lumen which can be used to introduce an at least partially fluid substance into a tissue. For example, the electrodes of the electrosensitisation module may comprise injector needles. Such needles may be used to administer a cell-death-facilitating agent to target cells at a target site, or saline to flush out dead cells, or other therapeutic agents to the target site.

The system is preferably adapted to deliver ultrasound and/or electric fields to a portion of a patient's body, for example, an organ. Accordingly, either or both of the ultrasound generating module and the electrosensitisation module may comprise a head portion which may be moved so that it is capable of being positioned close to the target to be ablated. Alternatively, a probe may be provided for positioning close to the target, suitably, an internal target. For example, if cells in the liver are to be targeted, an ultrasound probe may be positioned on the patient's abdomen so that ultrasound is substantially delivered to the liver. The head portion or probe may be connected by a suitable connection such as a cable to the rest of the device.

In another embodiment, the electrosensitisation module is capable of generating an electric field as a stimulus to disrupt an already sensitised cell, for example, an ultrasound sensitised cell. In this embodiment therefore, the electrosensitisation module may be used to disrupt the cell, while the ultrasound module may be used to sensitise the cell.

In a particularly, preferred aspect, the electrosensitising module and/or ultrasound module of the system are activatable by use of a hand held control unit or foot pedal which is communication with the processor and the operating parameters of either or both modules can be controlled through the use of the control unit.

The invention is further described, for the purpose of illustration only, in the following examples.

EXAMPLES

The invention will now be further illustrated with reference to the following examples. It will be appreciated that what follows is by way of example only and that modifications to detail may be made while still falling within the scope of the invention.

Example 1

The Effect of Low Intensity Ultrasound on Cells Treated with Pulses of 3.625 kV/cm The target cell line employed in these studies was a mouse friend leukaemic lymphoblast cell line (clone 707, ECACC no. 91112126 from the European Collection of Animal Cell Cultures) and is maintained in DMEM supplemented with 10% (v/v) foetal bovine serum. Cultures were maintained in a humidified 5% $CO_2$ atmosphere at 37° C. Cells were harvested by centrifugation, washed once in phosphate buffered saline (PBS) and suspended at a concentration of $1.065 \times 10^7$ cells/ml. 0.7 ml aliquots of this suspension were dispensed into electroporation cuvettes (0.4 cm electrode gap) together with 0.1 ml of PBS. Cuvettes were retained on ice and electroporated by delivering two pulses of 3.625 kV/cm at a capacitance of 1 $\mu$F. Cells were washed twice in PBS by centrifugation, resuspended in PBS containing $MgCl_2$ (4 mM) (PBS/Mg) and retained at room temperature for 30 minutes. Cells were washed twice in PBS/Mg containing 10 mM glucose, resuspended in the same buffer and retained at room temperature for 1 hour. A control population of cells was taken through the same procedure except that the electroporation step was omitted. Cell concentrations were adjusted to $1.4 \times 10^7$ cells/ml. 100 µl aliquots of cells were dispensed into microwells from a 96-well plate and positioned on a 3 MHz ultrasound head. Cells were exposed to ultrasound for 30 secs. Viability was determined using trypan blue.

The effect of increasing ultrasound power density on cell viability of normal cells and electrosensitised cells is shown in FIG. 1. The results demonstrate little or no effect on the normal control population of cells up to a power density of 1.5 W/cm$^2$ whereas cell viability decreased to almost 0 at 1 W/cm$^2$ following treatment of the electrosensitised population. It should be noted that cell viability is determined immediately after exposure to ultrasound. These results demonstrate that it is possible to sensitise the target cells to ultrasound conditions that have no effect on normal cells.

Example 2

The Effect of Low Intensity Ultrasound on Cells Exposed to Pulses of 1.875 and 2.5 kV/cm In order to determine whether or not the pulse electric field strength had any effect on susceptibility of the treated cells to low intensity ultrasound, 0.7 ml aliquots of cells ($0.8 \times 10^7$ cells/ml in PBS/Mg) were dispensed into electroporation cuvettes (0.4 cm electrode gap) together with 0.1 ml of PBS. Cuvettes were retained at room temperature and electroporated as described for Example 1 except that one population was treated with two pulses at 1.875 kV/cm and another was treated with two pulses at 2.5 kV/cm. Cells were transferred to PBS/Mg/glucose and retained at room temperature for 15 minutes. Samples were treated with ultrasound for 30 seconds and allowed to stand at room temperature for 1 hour prior to determining cell viability using trepan blue. A control population of cells was taken through the above treatment except that the electroporation event was omitted.

Figure 2:
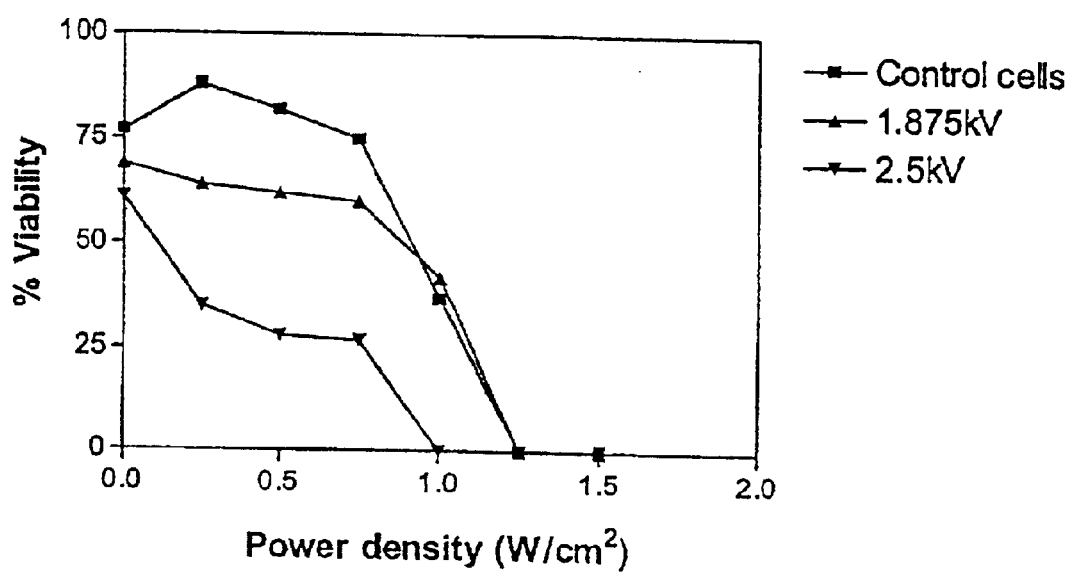
FIG. 2 is a graph of the effect of ultrasound on control cells (■), cells electrosensitised at 1.875 kV/cm at 1 $\mu$F (▲) and cells electrosensitised at 2.5 kV/cm (▼). Cell viability was determined one hour after exposure to ultrasound.

The effect of low intensity ultrasound on cells treated at both voltages is shown in FIG. 2. In this case, ultrasound had a limited effect on cell viability in the control population of cells up to 0.75 W/cm$^2$. At or above 1 W/cm$^2$ viability decreased dramatically in the control population. Ultrasound-mediated effects are observed in the population of cells treated with electric pulses of 1.875 kV/cm and viability is decreased at the lower ultrasound densities (0.25–0.75 W/cm$^2$). In the cells treated at 2.5 kV/cm$^2$, stronger effects are noted at all ultrasound power densities examined between 0.25 and 1 W/cm$^2$. The results confirmed that ultrasound sensitivity could be induced by exposure of cell populations to electric pulses. The results also demonstrate that susceptibility of cells to ultrasound increased with increasing electric field strength. The decrease in control cell viability following treatment with ultrasound in this experiment is more dramatic than that observed in Example 1 (FIG. 1) and this may be due to the increased resting time between ultrasound treatment and determination of cell viability described in Example 2.

Example 3

Sensitisation and Ultrasound Treatment of Cells Immobilised in Alginate Matrices In order to determine whether or not this sensitisation phenomenon could be achieved in a mass of cells, thereby mimicking a tumor mass, it was decided to embed the cells in an alginate matrix, expose the mass to electric pulses and subsequently expose it to ultrasound. Viability could then be determined using a modification of the MTT assay described previously (Rollan et al., *Bioprocess Eng.* 15: 47, 1996). To the above end 707 cells were harvested and suspended in 1% (w/v) sodium alginate (Keltone LV, Lot no. 35245A, Kelco, UK) at a concentration of $1.16 \times 10^7$ cells/ml. This suspension were added drop-wise to a calcium chloride solution (1.5% [w/v]) and beads (average vol. per bead=10 µl) retained in CaCl$_2$ for 15 minutes. Beads were subsequently rinsed in PBS and dispensed into electroporation cuvettes (30 beads/cuvette) together with 0.5 ml PBS. Two electric pulses of 2.5 kV/cm at a capacitance of 1 µF were delivered to each cuvette and cells were immediately transferred to culture medium. Aliquots of 5 beads were dispensed into the wells of a 96-well plate and exposed to ultrasound at 0.75 and 1.5 W/cm$^2$ at 3 MHz for 40 seconds. Beads were then placed in an incubator at 37° C. for 165 minutes. Medium was subsequently removed and the beads were washed once in PBS. 1 ml aliquots of MTT (1 mg/ml in PBS) were added to each sample of beads and these were retained at 37° C. for 1 hour. The MTT was then removed from the beads and 0.5 ml of NaOH (1M) added to each sample. Viability of cells in the beads was determined by measuring the absorbance of the resulting solution at 520 nm using spectophotometry. Control samples consisted of immobilised cells taken through the procedure with the exception of exposure to either electric pulses or ultrasound.

Figure 3:
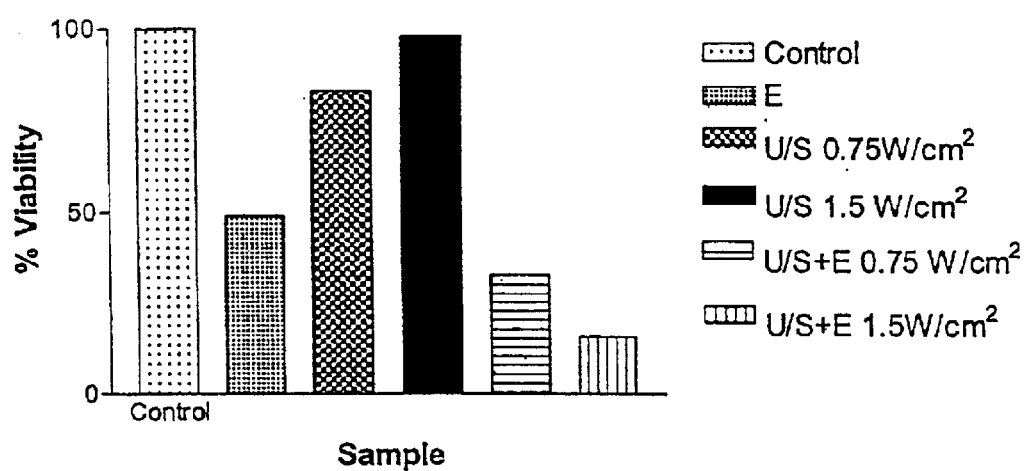
FIG. 3 is a bar chart showing the effect of ultrasound on the viability of control and electrosensitised cells immobilised in calcium alginate matrices in one embodiment of the invention.

The results from these experiments are shown in FIG. 3 and they demonstrate that ultrasound exposure at either 0.75 or 1.5 W/cm$^2$ had a very limited effect on control cells which had not been exposed to the electric pulses. Exposure of cells to electric pulses in the absence of ultrasound treatment resulted in a 50% decrease in viability. However, treatment of electro-sensitised cells with ultrasound at both power densities had dramatic effects on cell viability where treatment of samples at 1.5 W/cm$^2$ resulted in an 84% reduction in cell viability. It is important to note that the same power density had little or no effect on cell viability in the control sample. The results presented here demonstrate that a mass of cells may be sensitised to ultrasound using electric pulses and suggests that this may also be the case in a tissue mass in vivo.

The above results demonstrate that subjecting cell populations to electric fields in culture render those cells sensitive to low intensity ultrasound.

The following examples demonstrate that when tissue masses are treated with electric fields in vivo, those tissues are sensitive to low intensity ultrasound. These examples make use of a mouse tumor model known as RIF-1 (Twentyman et al., 1980, *J. Natl. Cancer Inst.* 64: 595–604). In Example 4, tumor cells were treated in vitro and these treated populations were then employed to inoculate animals. The development of tumors was monitored. In Example 5, animals were inoculated with the cells and the tumors which developed were treated with electric fields in vivo and subsequently with ultrasound.

Example 4

Tumor Development Following Electrosensitisation and Ultrasound Treatment of Tumor Cells in Vitro In this experiment RIF-1 cells were treated with electric fields, ultrasound or a combination of both, and the ability of the treated populations to induce tumor growth was assessed.

The target cells were grown in RPMI 1640 medium supplemented with 10 (v/v) foetal bovine serum and 1% penicillin/streptomycin stock (5000 µg/ml and 5000 g/ml, respectively) and in a 5% $CO_2$ humidified atmosphere. Cells were cultured to confluence and then harvested following treatment with trypsin-EDTA (0.005% and 0.002% [w/v], respectively). Cell concentrations were adjusted to $1 \times 10^6$ cells/ml in phosphate buffered saline and 0.8 ml aliquots are treated with (i) electric fields alone [1 kV/cm, double pulse at 1:F], (ii) ultrasound [1.25 $W/cm^2$ at 3 MHz for 30 sec.] and (iii) electric fields were followed immediately by treatment with ultrasound. Control populations consisted of cells at the same concentration without treatment. These cell populations were then used to inoculate 8-week old male C3H mice by intradermal injection of 0.1 ml into the rear dorsum of each animal. Tumor volume was calculated from the geometric mean of the diameter measured in 3 dimensions using the formula $4/3 \pi r^3$.

Figure 5:
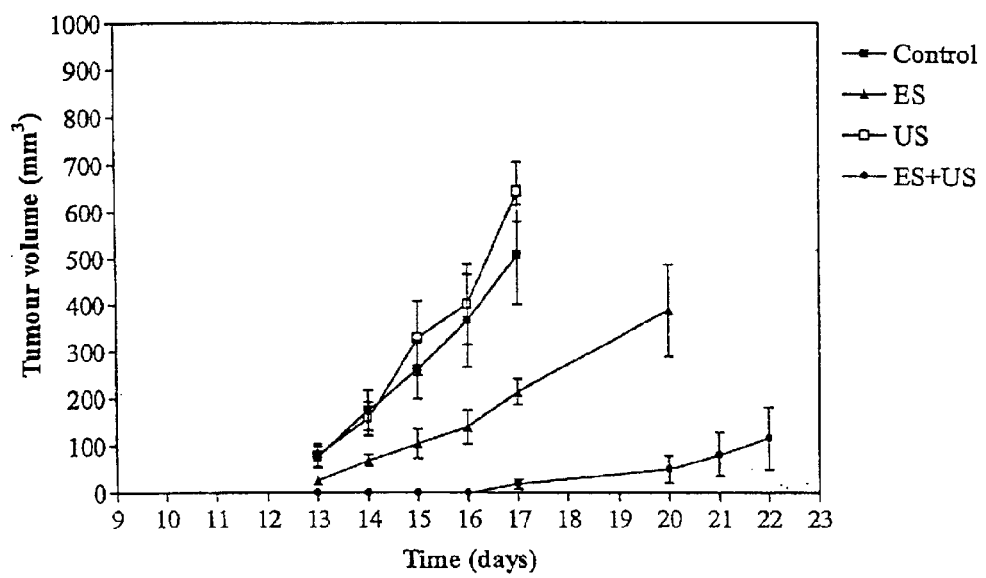
FIG. 5 is a graph illustrating the induction of tumors in C3H mice following treatment of a RIF-1 cell line with electric fields (▲), ultrasound (□), and electric fields in combination with ultrasound (●). Control populations of cells are those which receive no treatment (■). The x-axis represents time measured in days and the y-axis represents tumor volume measured in mm$^3$.

The results are shown in FIG. 5 and they demonstrate that while ultrasound has little or no effect on the ability of the cells to induce tumor growth, electrosensitisation does have a significant effect in this regard. The latter effect has been shown in for example Mir et al., 1991, *Eur J. Cancer* 27: 68–72.

However, most notably, tumors derived from the cells which receive the combined electric field and ultrasound failed to give rise to tumors until day 17. These results demonstrate that the combined treatment has the most dramatic effect on induction of tumor formation and a degree of synergy between treatments.

Example 5

Effect of Continuous Wave and Pulse Wave Ultrasound on Electrosensitised Tumor Cells in Vivo In this series of experiments tumors were induced in animals and these were employed as targets to determine the effects of in vivo treatments using electric fields, ultrasound (both continuous wave and pulsed) and combined treatments with electric fields followed by ultrasound.

To this end animals were inoculated with RIF-1 tumor cells as described above. When tumors reached an average volume of 50 $mm^3$ they were either untreated (control), treated with electric fields (set voltage=1.66 kV/cm and delivered voltage=1.33 kV/cm using a BTX 630 system together with Tweezertrodes, 7 mm), ultrasound on continuous wave emission at 3 MHz and at 0.7 $W/cm^2$, ultrasound on pulsed wave emission at 3 MHz at 1.8 $W/cm^2$ (duty cycle of 35%) and combinations of the electric field followed immediately by each form of ultrasound. Tumor growth was monitored by measuring tumor volume and this was determined as described above.

Figure 6:
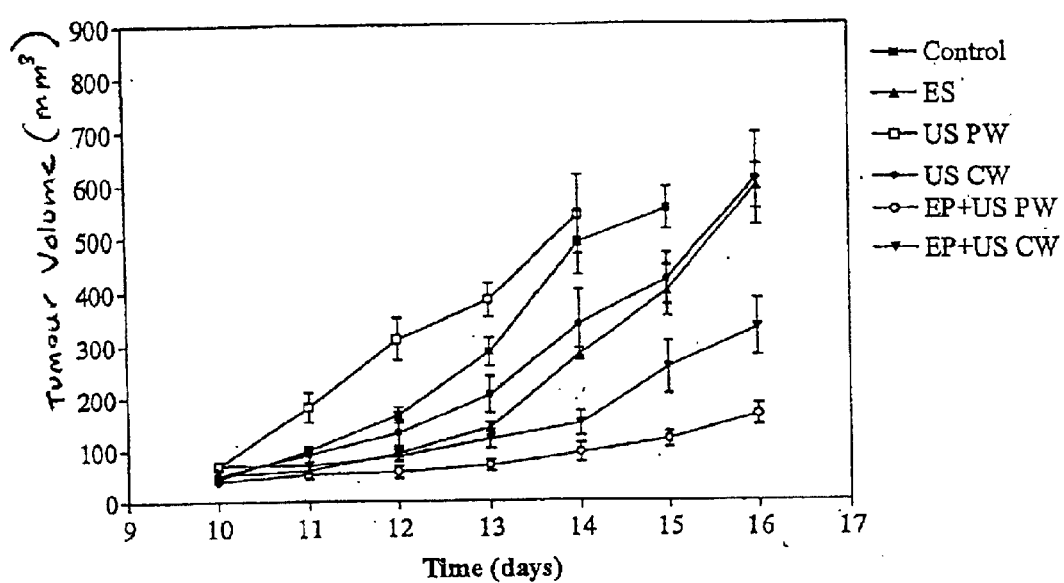
FIG. 6 shows the effect of the method according to the invention in one embodiment on the ablation of RIF-1 tumors in situ in mice upon exposure to an electric field (▲), pulsed wave ultrasound (□), continuous wave ultrasound (●), an electric field with continuous wave ultrasound (▼) and an electric field with exposure to pulsed wave ultrasound (○). Continuous wave ultrasound was delivered at 0.7 W/cm$^2$ at 3 MHz for 2 minutes, while pulsed wave ultrasound was delivered at 1.8 to 1.9 W/cm$^2$ at 3 MHz for 2 minutes at a 35% setting. Electric fields were delivered at 1.333 kV/cm. Control tumors (■) receive no treatment. The x-axis represents time measured in days and the y-axis represents tumor volume measured in mm$^3$.

The results are shown in FIG. 6 and they demonstrate that pulsed wave ultrasound treatment alone has no effect on tumor growth. Both electric field treatment alone and continuous wave ultrasound alone appear to have a slight effect on tumor growth. Notably, the combined treatments of electric field and each type of ultrasound show the greatest inhibition of tumor development.

In tumors which are treated with electric fields combined with ultrasound, those treated with pulsed wave ultrasound exhibit the greatest response, although the negative effects on growth following combined treatment with continuous wave ultrasound are also significant. It should be noted, however, that in terms of total energy delivered to the cells, pulsed wave ultrasound appears to be slightly more efficient than continuous wave (78 $J/cm^2$ for pulsed wave ultrasound versus 84 $J/cm^2$ for continuous wave ultrasound).

These results demonstrate that tumors treated with electric pulses in vivo are rendered sensitive to relatively low intensity ultrasound.

Example 6

Effect of Higher Intensity Continuous Wave and Pulse Wave Ultrasound on Electrosensitised Tumor Cells in Vivo Animals were inoculated with RIF-1 tumor cells, tumors treated, and tumor growth monitored as described above in Example 5. Treatment comprised electric fields of 1.33 kV/cm, ultrasound on continuous wave emission at 3 MHz and at 1.25 $W/cm^2$ for 2 minutes, ultrasound on pulsed wave emission at 3 MHz at 2.5 $W/cm^2$ for 2 minutes (35% continuous wave) and combinations of the electric field followed immediately by each form of ultrasound. Untreated cells were used as control, as above.

Figure 7:
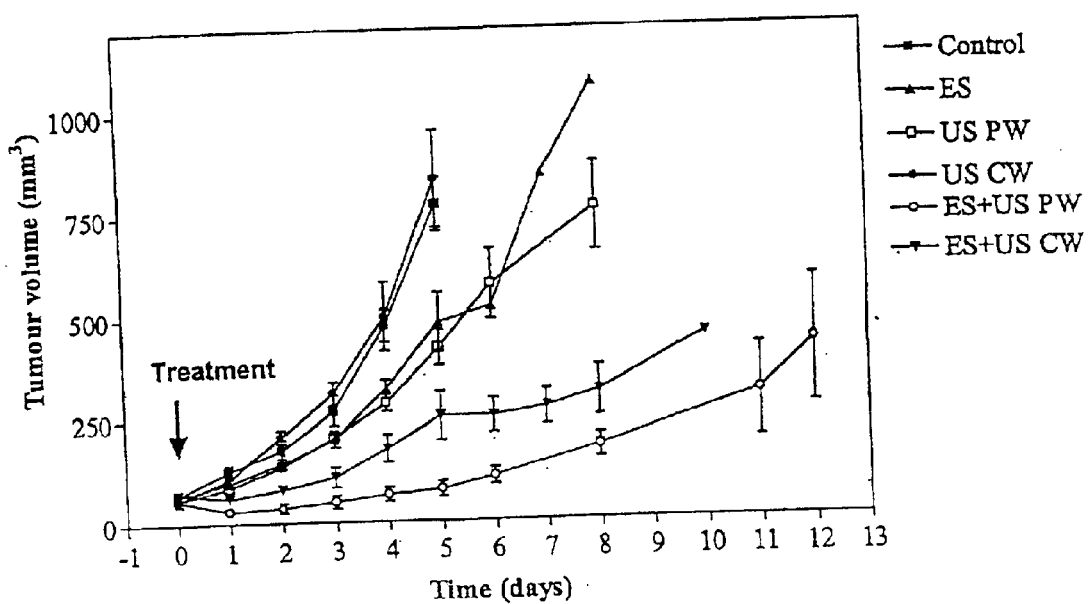
FIG. 7 shows the effect of the method according to the invention in one embodiment on the ablation of RIF-1 tumors in situ upon exposure to an electric field (▲), pulsed wave ultrasound (□), continuous wave ultrasound (●), electric field plus continuous wave ultrasound (▼) and electric fields plus pulsed wave ultrasound (○). Continuous wave ultrasound is delivered at 1.25 W/cm$^2$ at 3 MHz for 2 minutes, while pulsed wave ultrasound is delivered at 2.5 W/cm$^2$ at 3 MHz for 2 minutes at a 35% setting. Electric fields are delivered at 1.33 kV/cm. Control tumors (■) receive no treatment. The x-axis represents time measured in days and the y-axis represents tumor volume measured in mm$^3$.

The results are shown in FIG. 7 and they demonstrate that both pulsed wave ultrasound treatment and continuous wave treatment of electrosensitised cells are effective in slowing tumor growth. As before, pulsed wave treatment appears to be more effective than continuous wave treatment, even though the total energy delivered to the cells is 105 $J/cm^2$ for pulsed wave ultrasound versus 150 $J/cm^2$ for continuous wave ultrasound.

These results demonstrate that tumors treated with electric pulses in vivo are rendered sensitive to higher intensities of ultrasound.

Example 7

Treatment of Electrosensitised Tumors with Ultrasound at Various Times After the Electrosensitisation Event In the previous Examples ultrasound treatment immediately followed electrosensitisation. In order to examine the length of time tumors remain sensitive to ultrasound after the electrosensitisation event, tumors were electrosensitised in vivo and treated with ultrasound at various times after electrosensitisation. To this end tumors were inoculated into recipient mice as described above. Those tumors were electrosensitised by exposure to double pulses at 1.33 kV/cm. Tumors were then exposed to ultrasound (3.57 $W/cm^2$, 1 MHz using pulsed wave at 35% continuous wave for 2 min.) at 0, 0.5, 1, 2, 6 and 18 hours after electrosensitisation. Control animals remained untreated or were exposed to either electric field or ultrasound treatment alone. Tumor volume was monitored following treatment as described above.

Figure 8:
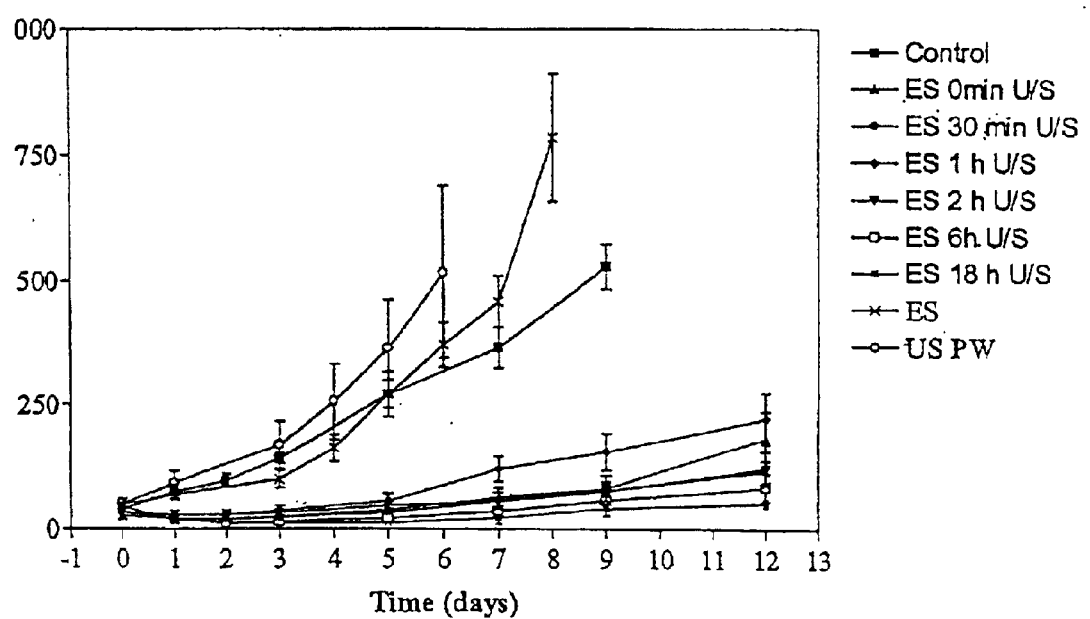
FIG. 8 is a graph showing results of treatment of electrosensitised tumors with ultrasound at 0 (▲), 0.5 (●), 1 (♦), 2 (▼), 6 (□) and 18 (*) hours after electrosensitisation. Control populations consisted of untreated (■) or treated with electric pulses (X) or ultrasound (○) alone. In these experiments error bars represent±SEM where n=3.

The results obtained from this experiment are shown in FIG. 8 and they demonstrate that significant effects are detected when ultrasound is delivered at all times post-electrosensitisation. These results demonstrate that cells remain electrosensitised to ultrasound for a considerable period of time following electrosensitisation. The results demonstrate that ultrasound does not necessarily have to be delivered immediately after electrosensitisation for cell ablation to take place.

Example 8

Induction of Apoptosis in Cells Treated with Electric Field and Ultrasound

In order to examine the molecular mechanism by which combined exposure of cells to electric fields and ultrasound induces cell death, cells were treated with a single pulse at various voltages and the effects of ultrasound on those cells were examined.

In addition to examining cell numbers remaining following treatment, the remaining population of cells were evaluated to determine whether cells were apoptotic or necrotic. To this end 707 cells were harvested and suspended in PBS at a concentration of $1.53 \times 10^6$ cells/ml. 0.8 ml aliquots were dispensed into electroporation cuvettes (0.4 cm electrode gap) and cells were treated with single electric pulses at a capacitance of 1 3 $\mu$F. Cells were harvested from cuvettes and each 0.8 ml aliquot was washed by centrifugation and resuspended in 2 ml of tissue culture medium containing fetal bovine serum. Each 2 ml aliquot was dispensed into a 2 ml well of a 24-well tissue culture plate. Control populations of cells were not treated with electric pulses but were dispensed into 2 ml wells. All samples were treated with ultrasound for 30 seconds at a power density of 1.25 W/cm$^2$ and using a 3 MHz ultrasound head (single pulse). Cells were then incubated at 37° C. for 21 hours in a a humidified 5% $CO_2$ atmosphere. Following incubation, cells were harvested and the proportion of cells which were either apoptotic or necrotic was determined by staining with an Annexin-V-FLOUS staining kit (Roche, UK). Following staining, cells were suspended in HEPES buffer and analysed using flow cytometry.

Figure 9:
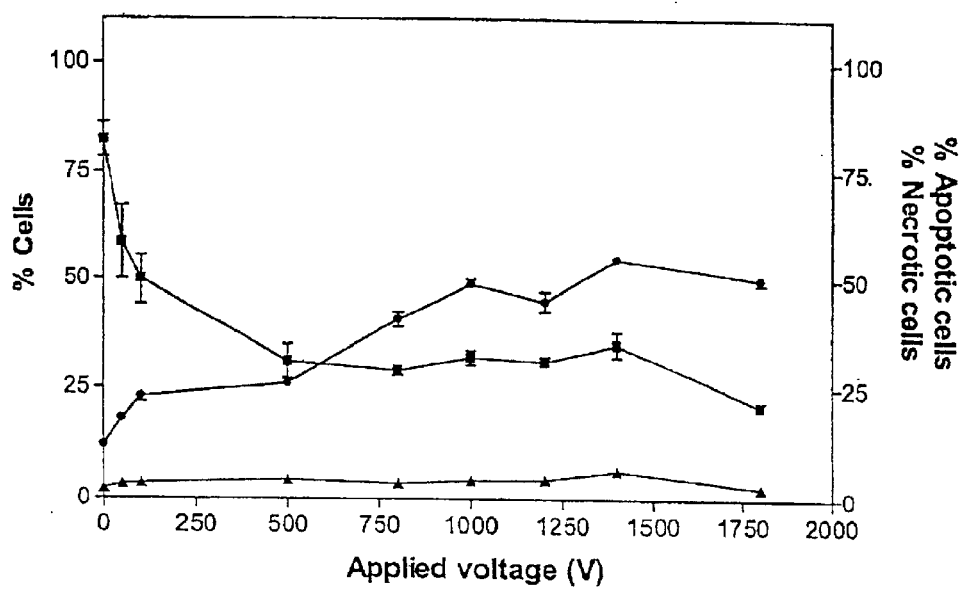
FIG. 9 shows the effect of combined treatment of 707 cells with increasing electric field strength (single pulse) and ultrasound at 1.25 W/cm$^2$ for 30 seconds using a 3 MHz ultrasound head according to one embodiment of the invention. Cell concentrations (■) were determined using a haemocytometer and the proportion of apoptotic (●) and necrotic (▲) cells in each population were determined by staining with Annexin V-FLUOS and propidium iodide followed by analysis using flow cytometry. Data reflect mean values±SEM of three experiments.

The results obtained are shown in FIG. 9. They demonstrate that ultrasound treatment alone results in an approximate 20% decrease in cell numbers. As the voltage is increased, combined treatment leads to a very significant decrease in cell numbers and this finally reaches a steady state above voltages of 750V.

In addition to examining cell numbers in remaining populations, the proportion of both apoptotic and necrotic cells in those surviving populations was examined. The results are also shown in FIG. 9 and they demonstrate that a significantly greater proportion of surviving cells remaining following treatment is apoptotic. These results demonstrate that treatment of electrosensitised cells with ultrasound facilitates the onset of apoptosis rather than necrosis.

Example 9

Induction of Apoptosis in Tumors Following Treatment with Combined Electric Fields and Ultrasound in Vivo As shown in previous Examples, treatment of target cell populations with electric fields and ultrasound leads to the induction of apoptosis in vitro. The objective of this Example was to demonstrate that combined treatment with electric fields followed by treatment with ultrasound in vivo leads to induction of apoptosis.

To the above end RIF-1 tumors are induced in C3H mice and these were employed as target tumors for combined treatments with electric pulses followed by ultrasound. Control animals received no treatment. Conditions used in electrosensitisation involved treatment with a double pulse regime consisting of 1.33 kV/cm and ultrasound treatment involved the use of pulsed wave ultrasound (35% continuous wave) at 1 MHz, 3.57 W/cm$^2$ for 2 minutes. Following treatment, tumors from control, untreated animals and those receiving treatment were harvested at 0, 6, 12, 18 and 24 hours post treatment. After harvesting tumors were fixed in 4% (w/v) paraformaldehyde overnight. Paraffin wax sections were then prepared for each sample and these were stained using the In situ cell death detection kit, TMR red (Roche, UK) according to the manufacturer's instructions. This staining method is based on terminal deoxynucleotidyl transferase nick end labelling (TUNEL) and apoptosis is indicated by fluorescent staining as observed using fluorescence microscopy.

Figure 10:
FIG. 10 shows induction of apoptosis in vivo, following treatment with electric fields and ultrasound according to one aspect of the invention. Sections from control (Column C) and treated animals (Column T) are stained for apoptosis. Panels from sections harvested at 0, 6, 12, 18 and 24 hours are displayed in descending order in each column. The panel at the bottom of the figure represents a positive control generated by DNAse I treatment of sections prior to staining.
Figure 10:
Figure 10:
Figure 10:
Figure 10:
Figure 10:
Figure 10:
Figure 10:
Figure 10:

The results obtained following examination with fluorescence microscopy are shown in FIG. 10. In control samples, the only sample that exhibits slight positive staining is the 24 hour sample and this may result from the inclusion of normal cells in the sections. All other control samples fail to yield a signal for apoptosis. In the treated samples, staining for apoptosis becomes strongly evident at 12 hours following treatment and clear signals are also evident at 18 and 24 hours (FIG. 10). The results clearly demonstrate that combined treatment with electric fields and ultrasound results in the onset of apoptosis.

Example 10

Effect of Treating Tumors with Ultrasound Prior to Electrosensitisation in Vivo.

In this series of experiments, tumors were established in mice as described above for Example 5. However in this Example, the tumors were treated with ultrasound prior to treatment with electric fields.

In this study animals were inoculated with RIF-1 tumors as described above. Tumors were then treated with ultrasound (2 minutes) at 1 MHz using a power density of 1.25 W/cm$^2$ at continuous wave and 3.57 W/cm$^2$ at pulsed wave (35% continuous wave) delivery mode. Tumors were then treated immediately with electric fields (double pulse using set voltage=1.66 kV/cm using a BTX 630 system together with Tweezertrodes, 7 mm). Tumor growth was monitored by measuring tumor volume and this was determined as above.

Figure 11:
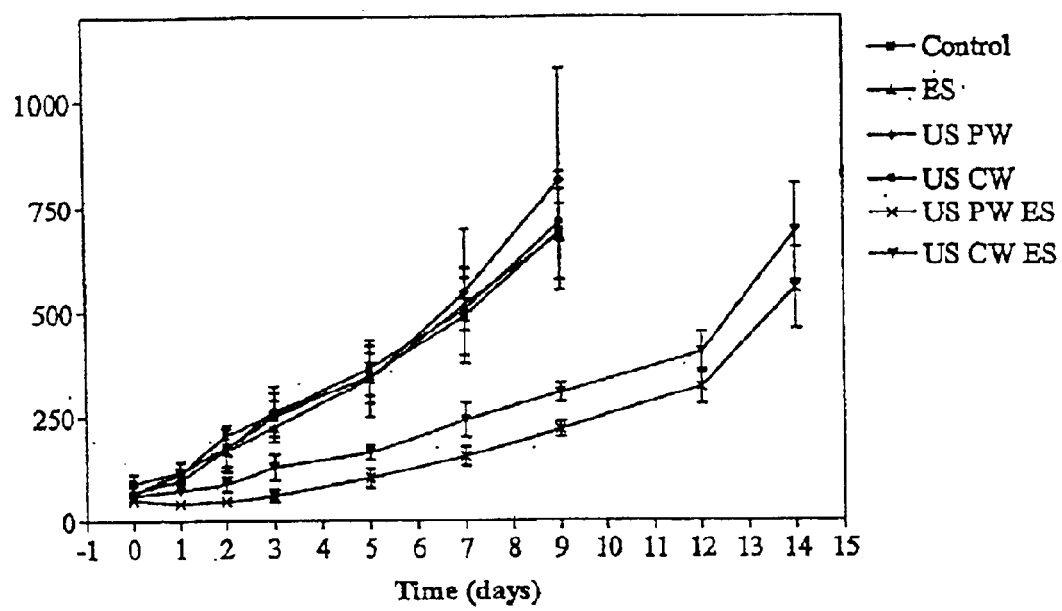
FIG. 11 shows the effect of treating tumors with ultrasound prior to electric fields according to one aspect of the invention. Groups of animals used in experiments consist of control untreated (■), electrosensitised (▲), ultrasound using pulsed wave (♦), ultrasound using continuous wave (●), pulsed wave ultrasound followed by electric fields (X) and continuous wave ultrasound followed by electric fields (▼). In each group n=4 and the error bars represent+SEM.

The results are shown in FIG. 11 and they demonstrate that treatment of tumors with ultrasound prior to electric fields also has an inhibitory effect on tumor growth. In addition, the inhibitory effect obtained using pulsed wave ultrasound is again greater than that observed using continuous wave ultrasound.

Surprisingly, the results demonstrate that the advantage associated with the use of combined treatment with electric fields and ultrasound in terms of tumor treatment is realised whether ultrasound is delivered prior to or following treatment with electric fields.

Example 11

Effect of Low Voltage Direct Current Electricity Treatment

Relatively intense electric fields were employed in the above examples. However, anti-tumor effects have also been demonstrated following treatment of tumors with low voltage/direct current (DC) alone (Nordenstrom, 1989, *Am. J. Clin. Oncol.* 12: 530–536; Wojcicki et al., 2000, *Med. Sci. Monit.* 6: 498–502). It was decided to investigate whether such low voltage/DC would render tumors or other cells hypersensitive to relatively low intensity ultrasound.

RIF-1 tumors were established in C3H recipient mice as described above. Needles were then horizontally inserted on each side of the tumors and electrodes attached to the needles. A constant current of 5 mA was established across the needles for a period of 15 minutes and cells were treated immediately with ultrasound at 3.75 W/cm$^2$ for a period of 3 minutes. During the treatment, the electric field strength ranged from 10 to 20 V/cm, with the field strength increasing as treatment progressed. Control animals were treated with electric current alone. Tumor volume was then monitored as described above.

Figure 12:
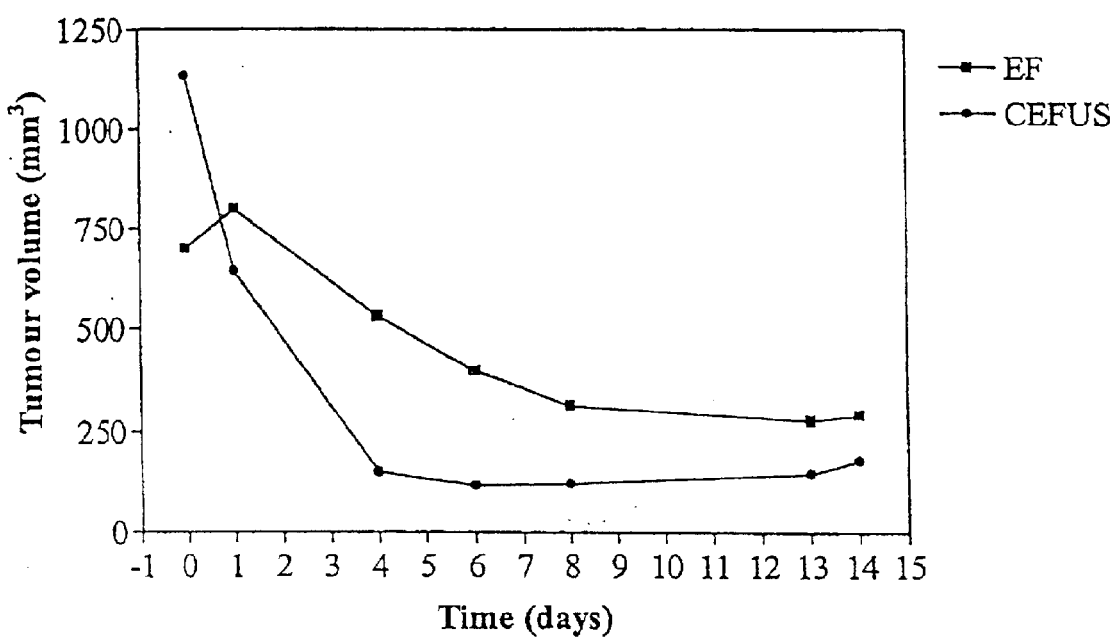
FIG. 12 shows the effect of direct electric current (■) and direct electric current together with ultrasound (●) on tumor volume.

The results are shown in FIG. 12 and they demonstrate that in the animal that is treated with electric current alone, the tumor volume decreased significantly over the time period examined and reached a minimum at 13 days. This also occurred in the animal that was treated with both electric current and ultrasound. However, the rate at which tumor volume decreased was significantly higher. In this case, tumor volume reached a minimum within 4–6 days.

It should be noted that the starting tumor size in this experiment was much greater than that in other studies described previously and in this context, the decrease in tumor size observed here was very dramatic. These results demonstrate that, although electrosensitisation of tumors to relatively low intensity ultrasound was achieved using pulses of high electric field strength, this phenomenon also occurs using strategies employing low electric field strengths with direct current. This observation broadens the degree of utility of the invention, particularly in cases where large areas of tissue may need to be sensitised.

Example 12

Treatment of Tumors with Direct Current Together with Ultrasound at 5 W/Cm$^2$ and 1 Mhz The objective of the experiments in this Example was to examine the effects of ultrasound at increased intensity on direct current-electrosensitised tumors. To this end, RIF-1 tumors were established in recipient C3H mice as described above and treated with (i) direct current alone at 5 mA for 5 minutes, (ii) pulsed ultrasound alone at 5 W/cm$^2$ for 2 minutes at 35% continuous wave, and (iii) direct current plus pulsed ultrasound using the conditions listed above. Tumor volume was measured as described previously. In addition, the growth of control, untreated tumors was also monitored.

Figure 13:
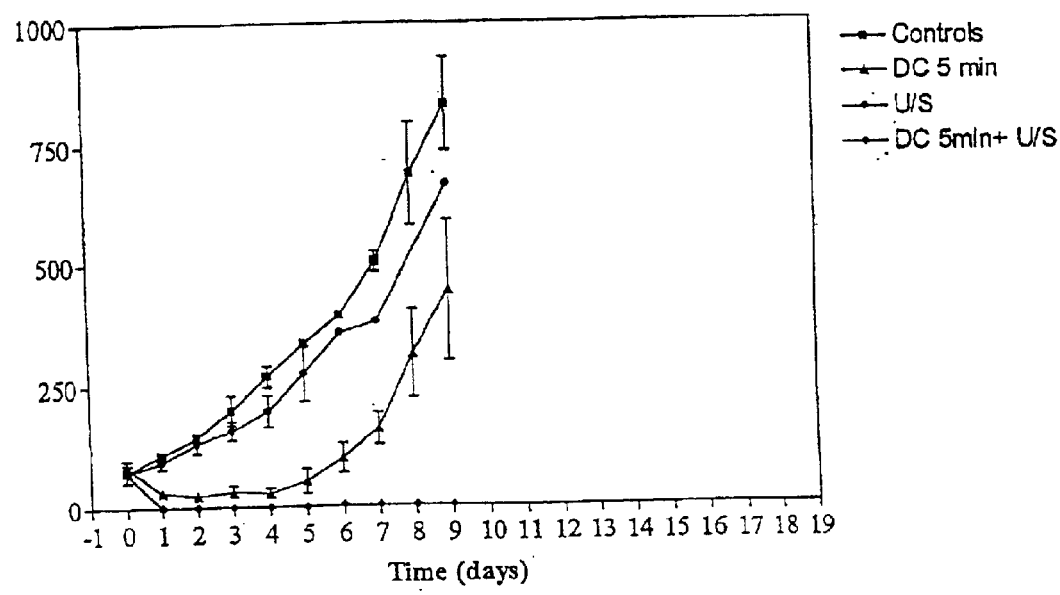
FIG. 13 shows the effect of treatment of RIF-1 tumors with ultrasound(●), direct electric current (▲) and combined direct electric current with ultrasound (♦). Control animals are untreated (■). Error bars represent±SEM where n=2.

The results are shown in FIG. 13 and they demonstrate that treatment with direct electric current leads to a decrease in tumor volume, although this begins to increase again at days 4 to 5. Treatment with ultrasound has a slight effect on tumor growth although at no stage is a reduction in tumor volume detected. In the group of animals receiving the combined treatment with direct current and ultrasound, complete regression was observed and this continued to be the case within the time period examined. The results again demonstrate that combined treatment of tumors with direct electric current and ultrasound leads to dramatic tumor regression.

Each of the applications and patents mentioned above, and each document cited or referenced in each of the foregoing applications and patents, including during the prosecution of each of the foregoing applications and patents ("application cited documents") and any manufacturer's instructions or catalogues for any products cited or mentioned in each of the foregoing applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the invention.

What is claimed is:

1. A method for selectively disrupting one or more target cells at a target site comprising a plurality of cells comprising: (a) exposing the one or more cells to an electric field; and (b) exposing the one or more cells to ultrasound; wherein said exposing in steps (a) and (b) disrupts said one or more target cells, wherein said one or more target cells comprise tumor cells, wherein said target site is within the body of an organism, wherein said target site is accessed using a medical access device which brings a source of electrical energy and ultrasound energy in sufficient proximity to the target site, to disrupt said one or more target cells and wherein said medical access device is selected from the group consisting of a catheter, an endoscope, and a laparoscope.

2. A method for selectively disrupting one or more target cells at a target site comprising a plurality of cells comprising: (a) exposing the one or more cells to an electric field; and (b) exposing the one or more cells to ultrasound; wherein said exposing in steps (a) and (b) disrupts said one or more target cells, wherein said target site comprises a wart, a papiloma, a psoriatic region of skin, a region of skin with eczema, or a mole.

3. A method for selectively disrupting one or more target cells at a target site comprising a plurality of cells comprising: (a) exposing the one or more cells to an electric field; and (b) exposing the one or more cells to ultrasound; wherein said exposing in steps (a) and (b) disrupts said one or more target cells, wherein said target site comprises an unwanted fatty deposit.

4. The method according to claim 3, wherein said fatty deposit is a lipoma.

5. The method according to claim 3 or 4, wherein said one or more target cells comprise adipose cells.

6. A method for selectively disrupting one or more target cells at a target site comprising a plurality of cells comprising: (a) exposing the one or more cells to an electric field; and (b) exposing the one or more cells to ultrasound; wherein said exposing in steps (a) and (b) disrupts said one or more target cells, wherein said exposing is used to debulk tissue.

7. A method for selectively disrupting one or more target cells at a target site comprising a plurality of cells comprising: (a) exposing the one or more cells to an electric field; and (b) exposing the one or more cells to ultrasound; wherein said exposing in steps (a) and (b) disrupts said one or more target cells, wherein said one or more cells are at the site of a wound.

8. A method for selectively disrupting one or more target cells at a target site comprising a plurality of cells comprising: (a) exposing the one or more cells to an electric field; and (b) exposing the one or more cells to ultrasound; wherein said exposing in steps (a) and (b) disrupts said one or more target cells, wherein said one or more cells are within a blood vessel.

9. A method for selectively disrupting one or more target cells at a target site comprising a plurality of cells comprising: (a) exposing the one or more cells to an electric field; and (b) exposing the one or more cells to ultrasound;

wherein said exposing in steps (a) and (b) disrupts said one or more target cells, wherein said target site comprises benign granulomatous tissue.

10. A method for selectively disrupting one or more target cells at a target site comprising a plurality of cells comprising: (a) exposing the one or more cells to an electric field; and (b) exposing the one or more cells to ultrasound; wherein said exposing in steps (a) and (b) disrupts said one or more target cells, wherein said one or more target cells comprise tumor cells, wherein said target site is within the body of an organism and wherein disrupted cells are removed from the body of the organism.

11. The method according to claim 10, wherein removal of cells is effected by immune response cells.

12. The method according to claim 11, further comprising administering to the organism an agent which modulates an immune response.

* * * * *